(12) United States Patent
Tanaka et al.

(10) Patent No.: US 6,744,057 B2
(45) Date of Patent: *Jun. 1, 2004

(54) CONVERGENT CHARGED PARTICLE BEAM APPARATUS AND INSPECTION METHOD USING SAME

(75) Inventors: Maki Tanaka, Yokohama (JP); Masahiro Watanabe, Yokohama (JP); Takashi Hiroi, Yokohama (JP); Hiroyuki Shinada, Chofu (JP); Taku Ninomiya, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/426,702

(22) Filed: May 1, 2003

(65) Prior Publication Data

US 2003/0197130 A1 Oct. 23, 2003

Related U.S. Application Data

(63) Continuation of application No. 10/012,400, filed on Dec. 12, 2001, now Pat. No. 6,559,459, which is a continuation of application No. 09/258,461, filed on Feb. 26, 1999, now Pat. No. 6,335,532, which is a continuation-in-part of application No. 09/132,220, filed on Aug. 11, 1998, now Pat. No. 6,107,637.

(30) Foreign Application Priority Data

Feb. 27, 1998 (JP) ............................. 10-046725

(51) Int. Cl.[7] .................. H01J 37/244; H01J 37/28
(52) U.S. Cl. .............. 250/491.1; 250/492.2; 250/310; 250/397; 250/398
(58) Field of Search .............. 250/491.1, 492.2, 250/310, 397, 398

(56) References Cited

U.S. PATENT DOCUMENTS

| | | | |
|---|---|---|---|
| 4,334,139 A | 6/1982 | Wittekoek et al. | |
| 4,468,565 A | 8/1984 | Blair et al. | |
| 4,788,431 A | 11/1988 | Eckes et al. | |
| 4,821,196 A | 4/1989 | Collopy et al. | |
| 5,008,705 A | 4/1991 | Sindledecker | |
| 5,166,529 A | 11/1992 | Ando et al. | |
| 5,216,235 A | 6/1993 | Lin | |
| 5,969,365 A | 10/1999 | Takemoto et al. | |
| 6,040,909 A | 3/2000 | Hasegawa et al. | |
| 6,335,532 B1 | 1/2002 | Tanaka et al. | |
| 6,559,459 B2 * | 5/2003 | Tanaka et al. | 250/491.1 |

FOREIGN PATENT DOCUMENTS

| | | |
|---|---|---|
| JP | 63-254649 | 10/1988 |
| JP | 5-258703 | 10/1993 |

* cited by examiner

Primary Examiner—Nikita Wells
(74) Attorney, Agent, or Firm—Antonelli, Terry, Stout & Kraus, LLP

(57) ABSTRACT

A convergent charged particle beam apparatus and method of detecting an electron beam image of a specimen in which a converged electron beam is irradiated and scanned over a surface of a specimen which is mounted on a movable stage and moves at least in one direction. An electron beam image of the surface of the specimen mounted on the stage is observed and a height of the specimen mounted on the stage is detected. A focus position of the electron beam is controlled in accordance with the height detected.

8 Claims, 26 Drawing Sheets

Region A (height za)

Region B (height zb)

Region C (height zc)

3 Sample wafer

Electron beam image in region A (height za)

Electron beam image in region B (height zb)

Electron beam image in region C (height zc)

Height detection optical system 22

13
Vacuum specimen chamber

Height detection optical system 22

23
Entrance window

13
Vacuum specimen chamber

Incidence angle small

Incidence angle large

Standard pattern for gain/offset adjustment 31b

Height detection optical system movable in parallel to electron optical system
22

Incident light intensity distribution 33
Reflected light intensity distribution 34
$2z \sin \theta$
35 Measurement error
32 Specimen surface
Variation in height Z
36 High reflectance area
37 Low reflectance area
38 Pattern boundary 45 Height detection value 36 High reflectance area
37 Low reflectance area In use of a wide slit In use of plural narrow slits

CONVERGENT CHARGED PARTICLE BEAM APPARATUS AND INSPECTION METHOD USING SAME

CROSS REFERENCE TO RELATED APPLICATION

This application a continuation application of Ser. No. 10/012,400, filed Dec. 12, 2001, now U.S. Pat. No. 6,559,459, which is a continuation of U.S. application Ser. No. 09/258,461, filed Feb. 26, 1999, now U.S. Pat. No. 6,335,532, which is a continuation-in-part application of U.S. application Ser. No. 09/132,220, filed Aug. 11, 1998, by some of the inventors herein, now U.S. Pat. No. 6,107,637, the subject matter of U.S. application Ser. No. 09/132,220 aforementioned applications being incorporated by reference herein.

BACKGROUND OF THE INVENTION

The present invention relates to a convergent charged particle beam apparatus using a charged particle beam such as an electron beam or ion beam for microstructure fabrication or observation and an inspection method using the same, and more particularly to an automatic focusing system and arrangement in the convergent charged particle beam apparatus.

As an example of an apparatus using a charged particle beam, there is an automatic inspection system intended for inspecting and measuring a microcircuit pattern formed on a substrate such as a semiconductor wafer. In defect inspection of a microcircuit pattern formed on a semiconductor wafer or the like, the microcircuit pattern under test is compared with a verified non-defective pattern or any corresponding pattern on the wafer under inspection. A variety of optical micrograph imaging instruments have been put to practical use for this purpose, and also electron micrograph imaging has found progressive applications to defect inspection by pattern image comparison. In a scanning electron microscope instrument which is specifically designed for critical-dimension measurement of line widths and hole diameters on microcircuit patterns used for setting and monitoring process conditions of semiconductor device fabrication equipment, automatic critical-dimension measurement is implemented through use of image processing.

In comparison inspection where electron beam images of corresponding microcircuit patterns are compared for detecting a possible defect or in critical-dimension measurement where electron beam images are processed for measuring such dimensions as pattern line widths, reliability of results of inspection or measurement largely depends on the quality of electron beam images. Deterioration in electron beam image quality occurs due to image distortion caused by deflection or aberration in electron optics, decreased resolution caused by defocusing, etc., resulting in degradation of performance in comparison inspection or critical-dimension measurement.

In a situation where a specimen surface is not uniform in height, if inspection is conducted on the entire surface area under the same condition, an electron beam image varies with each region inspected as exemplified in FIGS. 1(a)–1(d), wherein FIG. 1(a) shows a wafer with different regions A–C, FIG. 1(b) shows an in-focus image of region A and FIGS. 1(c) and 1(d) show defocused images of regions B and C, respectively. In inspection by comparison between the in-focus image of FIG. 1(b) and the defocused image FIG. 1(c) or FIG. 1(d), it is impossible to attain correct results. Further, since these images provide variation in pattern dimensions and results of edge detection on them are unstable, pattern line widths and hole diameters cannot be measured accurately. Conventionally, image focusing on an electron microscope is performed by adjusting a control current to an objective lens thereof while observing an electron beam image. This procedure requires a substantial amount of time and involves repetitive scanning on a surface of a specimen, which may cause a possible problem of specimen damage.

In Japanese Non-examined Patent Publication No. 258703/1993, there is disclosed a method intended for circumventing the abovementioned disadvantages, wherein an optimum control current to an objective lens for each surface height of a specimen is pre-measured at some points on the specimen and then, at the time of inspection, focus adjustment at each point is made by interpolation of pre-measured data. However, this method is also disadvantageous in that a considerable amount of time is required for measuring an optimum objective lens control current before inspection and each specimen surface height may vary during inspection depending on wafer holding conditions.

A focus adjustment method for a scanning electron microscope using an optical height detecting arrangement is found in Japanese Non-examined Patent Publication No. 254649/1988. However, since an optical element for height detection is disposed in a vacuum system, it is rather difficult to perform optical axis alignment.

In microstructure fabricating equipment using a convergent charged particle beam, focus adjustment of the charged particle beam has a significant effect on fabrication accuracy, i.e., focus adjustment is of extreme importance as in instruments designed for observation. Examples of microstructure fabricating equipment include an electron beam exposure system for forming semiconductor circuit patterns, a focused ion beam (FIB) system for repairing circuit patterns, etc.

In a scanning electron microscope, a method of measuring an optimum control current to an objective lens thereof through electron beam imaging necessitates attaining a plurality of electron beam images for detecting a focal point, thus requiring a considerable amount of time for focus adjustment. That is, such a method is not suitable for focusing in a short time. Further, in an application of automatic inspection or critical-dimension measurement over a wide range, focus adjustment at every point using the abovementioned method is not practicable, and it is therefore required to perform pre-measurement at some points before inspection and then estimate a height at each point through interpolation, for instance. FIG. 2 shows an overview of an electron-beam automatic semiconductor device inspection system to which the present invention is directed. In such an automatic inspection system, a specimen wafer under inspection is moved by means of stages with respect to an electron optical system thereof for carrying out wide-range inspection.

A semiconductor wafer to be inspected in a fabrication process may deform due to heat treatment or other processing, and a degree of deformation will be on the order of some hundreds of micrometers in the worst case. However, it is extremely difficult to hold the specimen wafer stably without causing interference with electron optics in a vacuum specimen chamber, and also it is impossible to adjust specimen leveling as in an optical inspection system using vacuum chucking.

Further, since a substantial amount of time is required for inspection, a specimen holding state may vary due to acceleration/deceleration in reciprocating stage movement, thereby resulting in a specimen surface height being different from a pre-measured level.

For the reasons mentioned above, there is a rather high degree of possibility that a surface height of a specimen under inspection will vary unstably exceeding a focal depth of the electron optical system (a depth of focus is generally on the order of micrometers at a magnification of 100×, but that necessary for semiconductor device inspection depends on inspection performance requirements concerned). For focus adjustment using electron beam images, a plurality of electron images must be attained at each point of interest with each stage being stopped. It is impossible to conduct focus adjustment continuously while detecting a height at each point simultaneously with stage movement for the specimen under inspection.

In an approach that focus adjustment using electron beam images is performed at some points on a specimen surface before the start of inspection, an amount of time is required for calibration before inspection. This causes a significant decrease in throughput as a size of wafer becomes larger. Since there is a technological trend toward larger-diameter wafers, a degree of wafer deformation such as bowing or warping will tend to be larger, resulting in more stringent requirements being imposed on automatic focusing functionality. Depending on the material of a specimen, exposure with an electron beam may alter an electric charge state on specimen surface to cause an adverse effect on electron beam images used for inspection.

In consideration of the above, it is difficult to ensure satisfactory performance in long-period inspection on a scanning electron microscope instrument using the conventional methods. Where stable holding of a specimen is rather difficult, it is desirable to carry out specimen surface height detection in a range of electron optical observation immediately before images are attained during inspection. Further, where inspection is conducted while each stage is moved continuously, specimen surface height detection must also be carried out continuously at high speed without interrupting a flow of inspection operation. For realizing continuous surface height detection simultaneously with inspection, it is required to detect a height of each inspection position or its vicinity at high speed.

However, if any element which affects an electric or magnetic field, e.g., an insulating or magnetic element, is disposed in the vicinity of an observation region, electron beam scanning is affected adversely. It is therefore impracticable to mount a sensor in the vicinity of electron optics. Further, since the observation region is located in the vacuum specimen chamber, measurement must be enabled in a vacuum. For use in the vacuum specimen chamber, it is also desirable to make easy adjustment and maintenance available. While there have been described conditions as to an example of an electron-beam inspection system, these conditions are also the same in a microstructure observation/fabrication system using an ion beam or any other convergent charged particle beam. Further, since there are the same conditions in such systems that images of an aperture, mask, etc. are formed or projected as well as in a system where a charged particle beam is converged into a single point, it is apparent that the present invention is applicable to charged particle beam systems comprising any charged particle beam optics for image formation/projection.

SUMMARY OF THE INVENTION

It is therefore an object of the present invention to provide an arrangement for detecting a surface height of an object item in an observation/fabrication region of charged particle beam optics or in its vicinity under vacuum at high speed without causing interference with the charged particle beam optics.

According to the present invention, there is provided a highly reliable system in which the object item can be observed/fabricated with its image being always in focus using surface height data thus detected.

According to an embodiment of the present invention, there is provided a height detector capable of detecting a surface height of an object item in an observation/fabrication region without causing interference with charged particle beam optics simultaneously with observation/fabrication and a system capable of carrying out observation/fabrication using a charged particle beam image formed in the charged particle beam optics in which focus adjustment can be made with height data obtained through the height detector. For enabling specimen height detection without causing interference with the charged particle beam optics, it is necessary to provide a height detector which can detect a surface height from a distant position apart from the charged particle beam optics. Further, for preventing an adverse effect on charged particle beam scanning, a height detection method must be arranged so that influence on electric and magnetic fields in the vicinity of a detection position will not vary with time. Additionally, since a specimen chamber is evaluated, the height detector must be usable under vacuum.

According to one aspect of the present invention, there is provided a height detector based on an optical height detection method in which light is projected to a height detection position slantwise and reflected light from a specimen surface is measured for height detection.

In accordance with the present invention, a convergent charged particle beam system comprises an electron beam source, an electron optical system unit for converging an electron beam emitted from the electron beam source into focus, a vacuum chamber unit having the inside thereof evacuated, a stage unit arranged in the inside of the vacuum chamber means so as to mount a specimen under inspection thereon and move the specimen along each plane, an electron beam image observation unit for observing an electron beam image of a surface of the specimen mounted on the stage unit in a manner that the electron beam converged by the electron optical system means is scanned over the surface of the specimen for irradiation and secondary charged particles produced from the specimen are detected, a height detecting unit for optically detecting a specimen surface height in a region irradiated with the electron beam scanned by the electron optical system means, a control unit for controlling a focal point of the electron beam converged by the electron optical system unit and a heightwise relative position of the specimen through use of resultant data detected by the height detecting unit, and a defect detecting unit for detecting a possible defect on the specimen by processing electron beam image data of the surface of the specimen observed by the electron beam image observation means in a state that the focal point of the electron beam and the heightwise relative position of the specimen are controlled by the control unit.

Further, in accordance with the present invention, there is provided an inspection method using a convergent charged particle beam system, comprising the steps of setting a specimen under inspection on a movable table inside a processing chamber, evacuating the processing chamber containing the specimen, scanning an electron beam emitted from an electron beam source while moving the movable table in the inside of the evacuated processing chamber to optically detect a height of a scanning-electron-beam-irradiated region on a surface of the specimen in an optical axis direction of the electron beam source, adjusting a surface height of the specimen in the optical axis direction according to resultant height data thus detected, scanning the electron beam emitted from the electron beam source for irradiation over the specimen thus adjusted in height while moving the movable table, detecting secondary charged particles produced from the specimen irradiated with the electron beam through scanning to attain a secondary charged particle image of the surface of the specimen, and inspecting the specimen using the secondary charged particle image thus attained.

These and other objects, features and advantages of the present invention will become more apparent from the following description when taken in conjunction with the accompanying drawings.

DESCRIPTION OF THE PREFERRED EMBODIMENTS

Figure 1A:
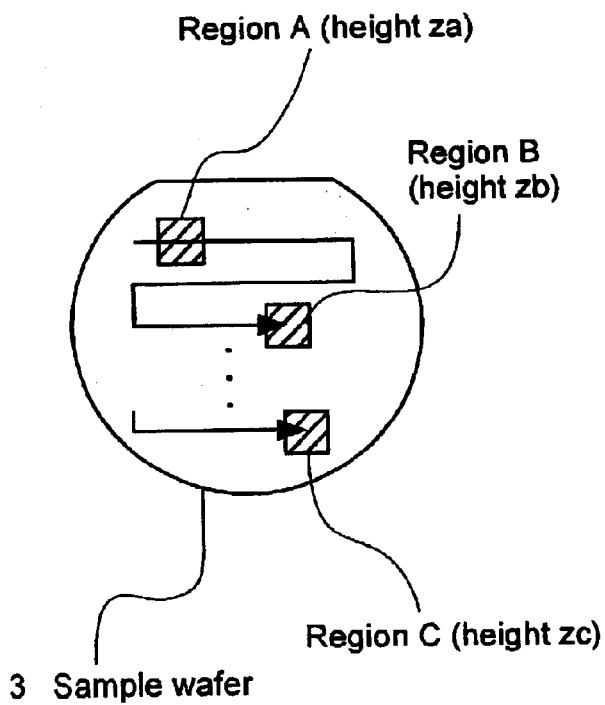
FIGS. 1(a)–1(d) show inspection of a wafer at different regions and electron beam images of the different regions.
Figure 1B:
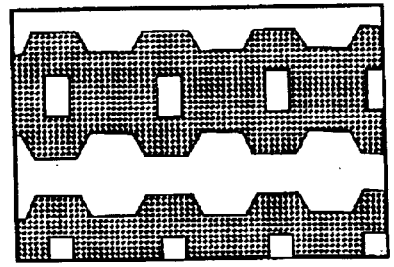
Figure 1C:
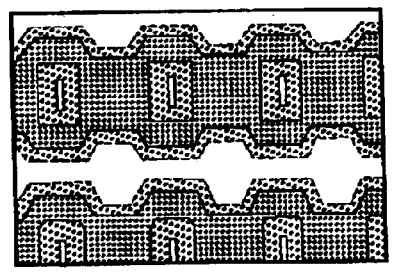
Figure 1D:
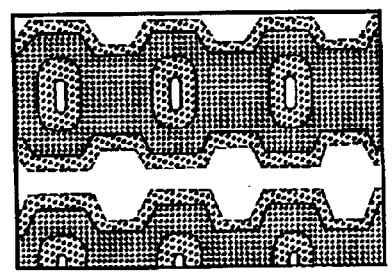
Figure 2:
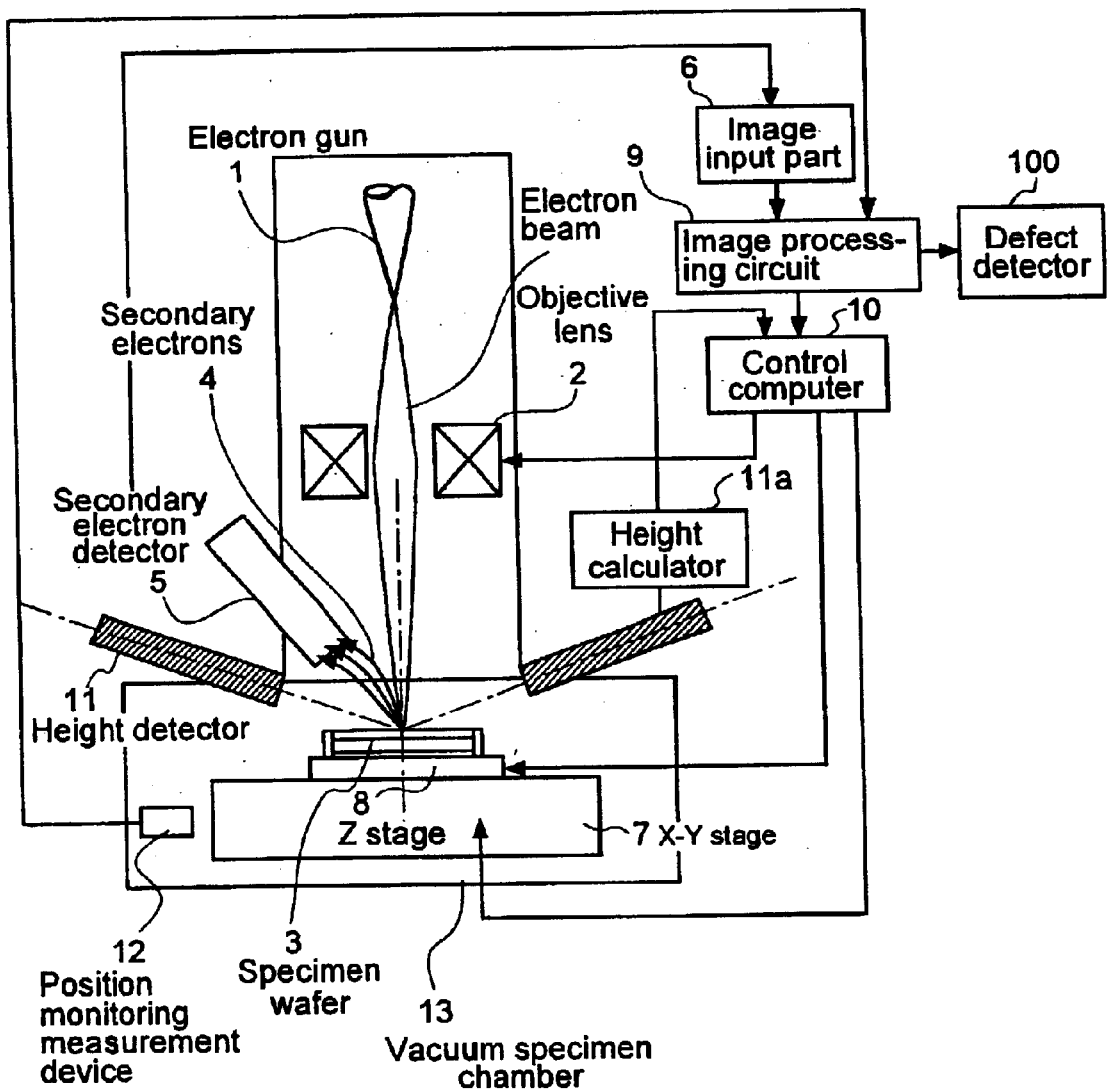
FIG. 2 is a schematic sectional view showing an exemplary structure of an automatic inspection system according to the present invention.

Referring now to the accompanying drawings wherein like reference numerals are utilized to designate like parts throughout the views, there is shown in FIG. 2 an overview of an automatic semiconductor device inspection system using electron beam images as an exemplary preferred embodiment of the present invention. In an electron optical system shown in FIG. 2, an electron beam emitted from an electron gun 1 is converged through an objective lens 2, and the electron beam thus converged can be scanned over a surface of a specimen in an arbitrary sequence. A signal of secondary electrons 4 produced on a surface of a specimen wafer 3 in irradiation with the electron beam is detected by a secondary electron detector 5, and then the secondary electron signal is fed to an image input part 6 as an image signal.

The specimen wafer under inspection can be moved by an X-Y stage 7 and a Z stage 8. By moving each stage, an arbitrary point on the surface of the specimen wafer is observable through the electron optical system. Electron beam irradiation and image input can be performed in synchronization with stage movement, which is controlled under direction of a control computer 10. A height detector 11 is of an optical non-contact type which does not cause interference with the electron optical system, and it can speedily detect a height of the specimen surface at or around an observation position in the electron optical system by a height calculator 11a. Resultant data of height detection is input to the control computer 10.

According to the height of the specimen surface, the control computer 10 adjusts a focal point of the electron optical system, i.e., a position of the Z stage, and it receives input of the image signal. Using the image signal input in a focused state and inspection position data detected by a position monitoring measurement device, defect judgment is carried out through comparison with a pattern pre-stored by an image processing circuit 9, a corresponding pattern at a location on the specimen wafer under inspection, or a corresponding pattern on a different wafer with a defect being detected by defect detector 100. While the automatic semiconductor device inspection system using secondary electron images is exemplified in FIG. 2, back scattered electron images or transmitted electron images may also be used for specimen surface observation instead of secondary electron images.

Figure 3:
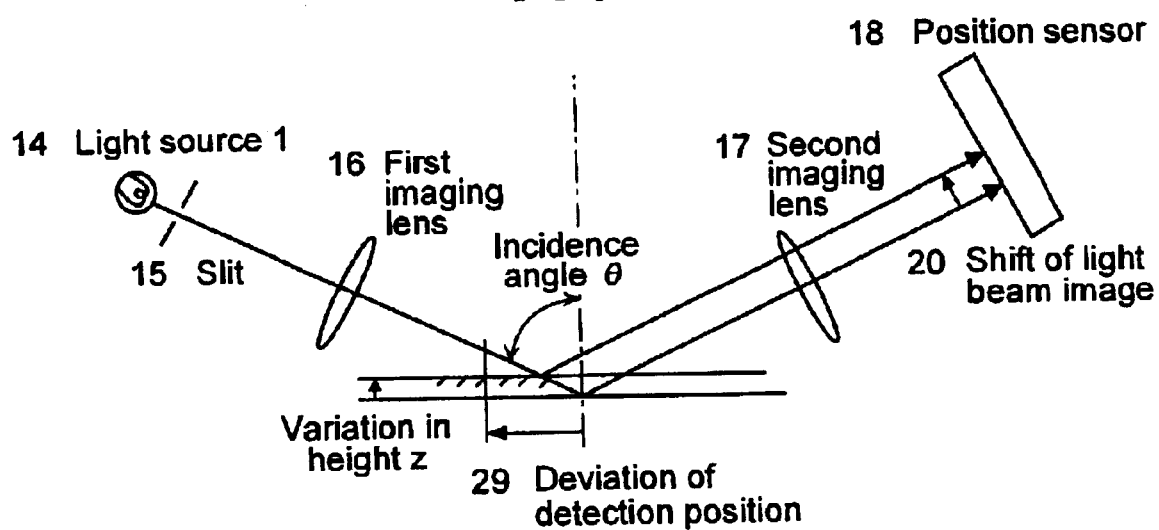
FIG. 3 is a schematic sectional view of a height detection optical system for illustrating a principle of height detection.

In the example shown in FIG. 2, a spot or slit light beam is projected onto the specimen surface, reflected light therefrom is imaged, and a position of a light beam image thus attained is detected for determining a height of the specimen surface (hereinafter referred to as a light-reflected position detecting method). More specifically, as shown in FIG. 3, the spot or slit light beam is projected onto the specimen surface at a predetermined angle of incidence so that its image is formed on the specimen surface, and reflected light thereof from the specimen surface is detected. Through conversion from specimen surface height variation to light beam image shift, a degree of light beam image shift is detected to determine a height of the specimen surface.

The height detector described above may also be applicable to different types of microstructure observation/fabrication systems using other convergent charged particle beams as in the inspection system exemplified in FIG. 2. The following exemplary preferred embodiments of the height detector are described as related to a microstructure observation system using a charged particle beam, but it is apparent that the height detector may also be applicable to a microstructure fabrication system using a charged particle beam. As will be apparent to those skilled in the art, the degradation in image quality in the microstructure observation system corresponds to the degradation in fabrication accuracy in the microstructure fabrication system. It is also apparent that the present invention is not limited in its application to a charged particle beam system in which a charged particle beam is converged to a single point. The present invention is further applicable to such microstructure fabrication systems that images of an aperture, mask, etc. are formed/projected, and it provides similar advantageous effects in these systems having image-forming charged particle optics. As an example of such microstructure fabrication systems, there is an electron beam lithography system using cell-projection exposure.

In the light-reflected position detecting method mentioned above, since a height detection optical element is not located directly above a detection position, a height in an observation region in a charged particle beam optical system can be detected simultaneously with observation by the charged particle beam optical system in a fashion that virtually no interference takes place. By making a height point detected by the height detector meet an observation region in the charged particle beam optical system, a surface height of an object item can be known at the time of observation. In this arrangement, through feedback of height data thus attained, observation can be conducted using a charged particle beam which is always in focus.

It is not necessarily required to provide such a condition that a desired observation region in the charged particle beam optical system meets a corresponding height point detected by the height detector, but rather it is just required that a surface height of the object is recognizable at the time of observation using vicinal height data attained successively. In use of the light-reflected position detecting method, optical parts may be arranged flexibly to some extent in optical system design, and it is therefore possible to dispose the optical parts to prevent interference with the charged particle beam optical system.

Figure 4:
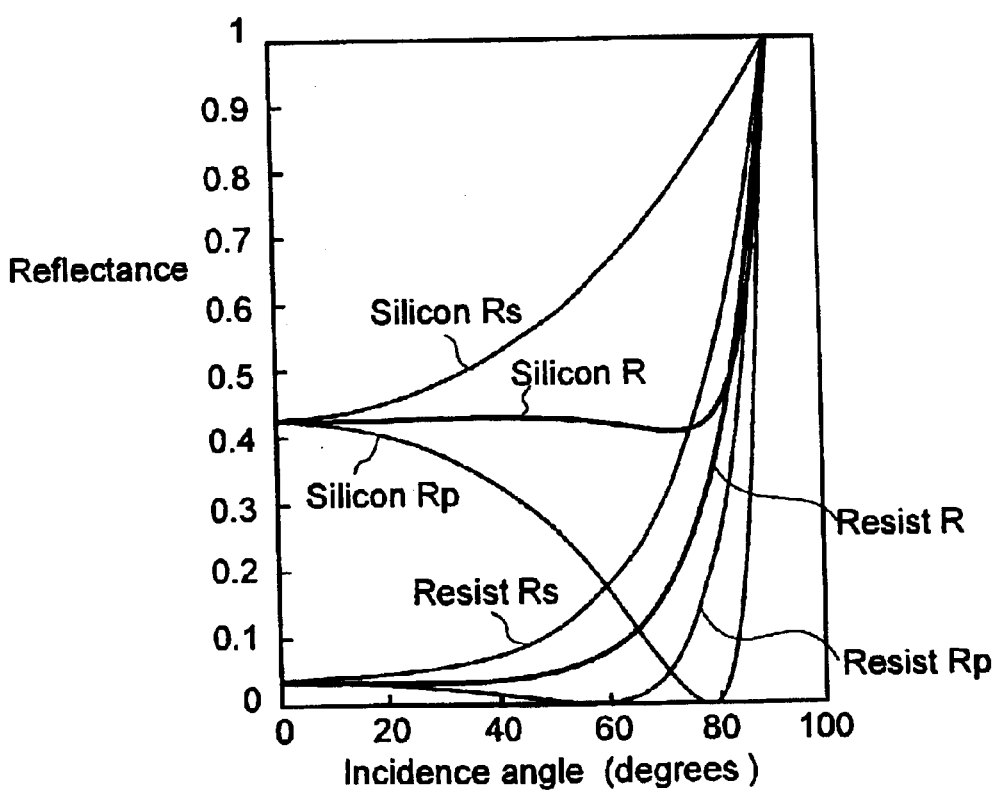
FIG. 4 is a graph showing variation in reflectance with respect to incidence angle on each material.

Disposition of the height detector in the light-reflected position detecting method is substantially limited by an angle of incidence on the object surface. In the light-reflected position detecting method, since a degree of incidence angle has an effect on height detection performance, an incidence angle cannot be determined only by part disposition in the system. FIG. 4 shows incidence angle dependency of surface reflectance of silicon and a resist which are representative materials used in formation of semiconductor wafer circuit patterns. A value of reflectance on specimen surface increases with an increase in incidence angle, and a difference in reflectance between materials decreases with an increase in incidence angle. This tendency characteristic also holds for other kinds of materials. Any difference in reflectance between materials causes nonuniform reflectance on the specimen surface, causing irregularity in distribution of the quantity of light detected. If irregular distribution of the quantity of light occurs in a detected slit image due to nonuniform reflectance of specimen surface pattern, an error takes place in slit position detection, resulting in a decrease in accuracy of height detection.

Referring to FIG. 3, a degree of light beam image shift is detected by a position sensor. Instead of the position sensor, a linear image sensor or any sensor capable of detecting a light beam irradiating position may also be used. For ensuring a proper S/N ratio in output of such a sensor, it is required to detect an adequate quantity of light. To provide a sufficient quantity of light for stable detection, it is desirable to increase the incidence angle. In principle, detection sensitivity in the light-reflected position detecting method become higher as the incidence angle with respect to the vertical increases. An adequate quantity of detected light can be ensured by providing an arrangement that the incidence angle is 60 degrees or more. More particularly, it has been determined that 70 degrees provides good results.

Exemplary preferred embodiments of disposition of optical parts in a height detection optical system are described in the following description wherein in general, if an insulator is located in the vicinity of a charged particle beam optical system, a possible charge build-up in the insulator affects an electric field around it to cause an adverse effect on charged particle beam deflection, resulting in degradation in image quality. Since such a charging effect varies with time as a charged condition changes, compensation for it is difficult practically.

For attaining a stable charged particle beam image, disposition of an insulator such as a lens at a position encountered with the charged particle beam must be avoided. If the insulator is coated with a conductive film and disposed at a position sufficiently apart from the charged particle beam optical system, an adverse effect may be reduced. A degree of requirement for preventing an adverse effect of the insulator (lens) on the charged particle beam optical system depends on specifications of the charged particle beam optical system such as visual field condition, accuracy, resolution, etc. According to the specifications of the charged particle beam optical system, a range influential on the charged particle beam optical system may be determined, and an optical path may be designed so that the insulator is not disposed in the influential range, thus preventing an adverse effect on the charged particle beam optical system.

Figure 5:
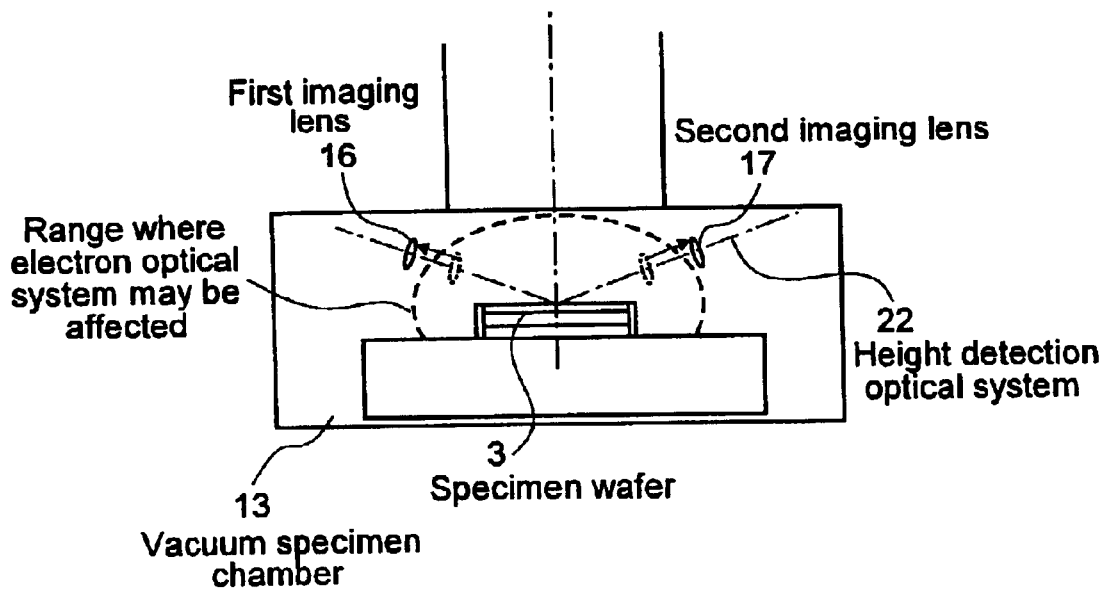
FIG. 5 is a schematic sectional view of a specimen chamber, showing an example of altered disposition of height detection optical system parts.

When a lens for the height detector is disposed in the periphery of the charged particle beam optical system, an effect on the charged particle beam can be presumed experimentally through computer simulation. The height detection optical system may be designed after determining a suitable mounting position of each lens as illustrated in FIG. 5. A distance between a surface of a specimen (imaging point) and each of lenses 16 and 17 facing the specimen may be adjusted by selecting lenses having a proper focal length.

Figure 6:
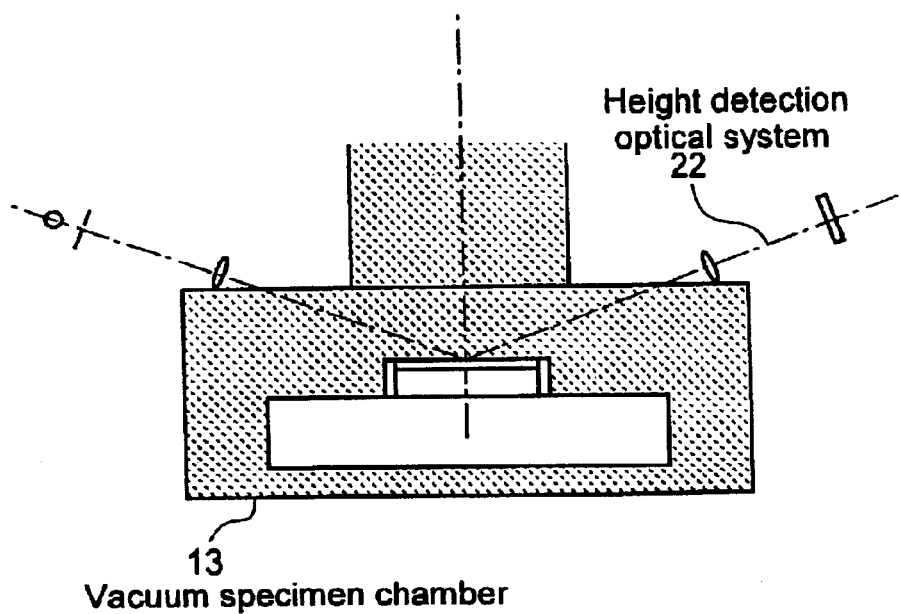
FIG. 6 is a schematic sectional view of a specimen chamber, showing an arrangement in which the height detection optical system parts are disposed outside the specimen chamber.
Figure 7:
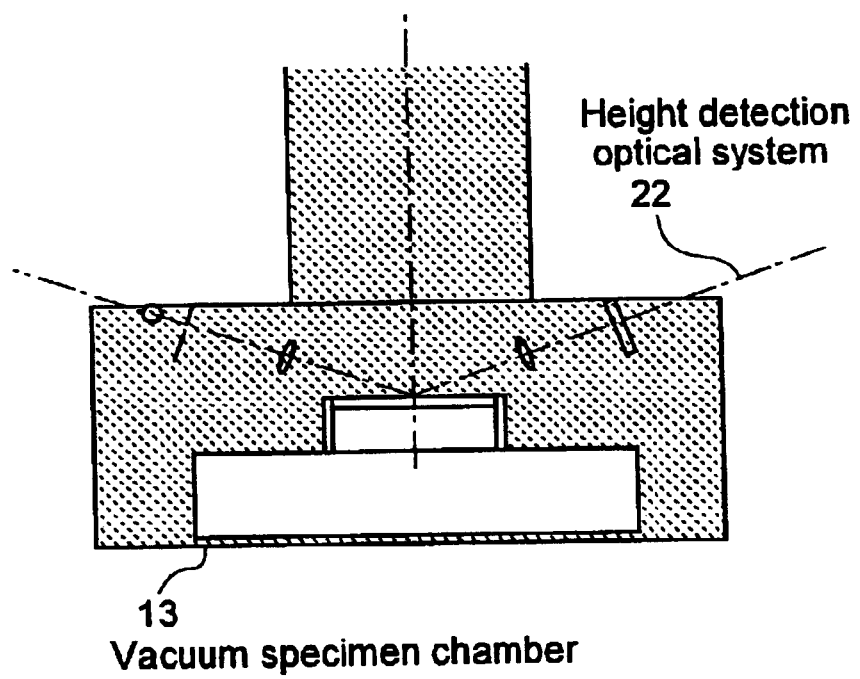
FIG. 7 is a schematic sectional view of a specimen chamber, showing an arrangement in which the height detection optical system parts are disposed inside the specimen chamber.

In the preferred embodiment mentioned above, each lens is disposed at a position which does not cause an adverse effect on the charged particle beam optical system. Further, as shown in FIG. 6, there may also be provided such an arrangement that the lenses and other parts of the height detection optical system can be located outside a vacuum specimen chamber 13 by increasing a distance between the specimen surface and each lens facing the specimen. On a casing between the inside of the vacuum specimen chamber 13 and the atmosphere, there may be provided a transparent window made of glass or the like. In this arrangement wherein the optical parts of the height detection optical system are disposed outside the vacuum specimen chamber, adjustment at the time of installation and maintenance thereafter will be easier advantageously than when the height detection optical system is disposed in a vacuum as shown in FIG. 7.

Figure 8:
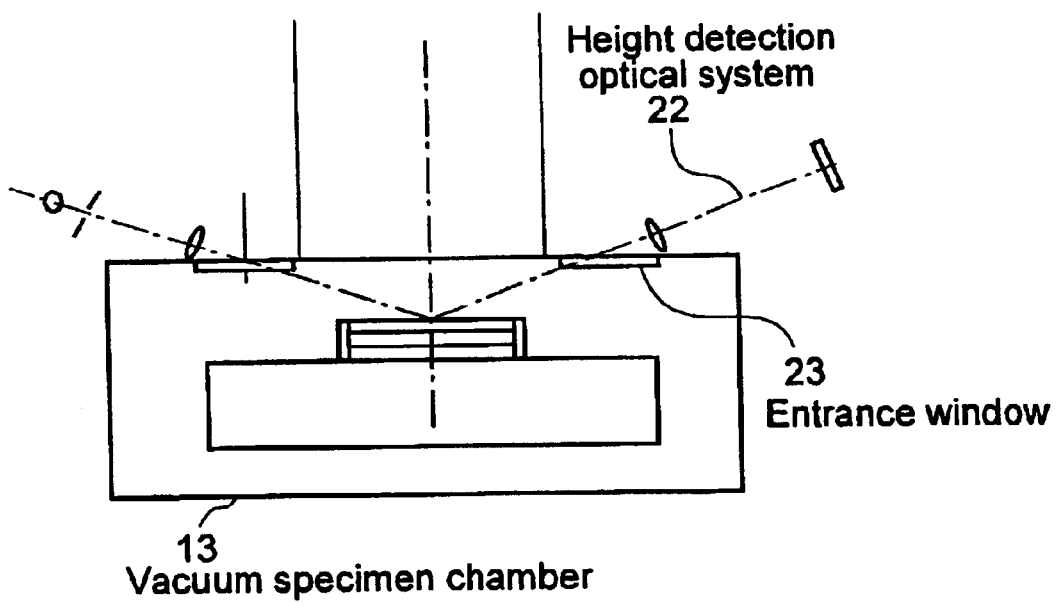
FIG. 8 is a schematic sectional view of a specimen chamber, showing an arrangement in which optical path windows are formed along a plane of an external top wall of the specimen chamber.

As in the preferred embodiment exemplified above, some or all of the optical parts of the height detection optical system may be arranged outside the vacuum specimen chamber. As illustrated in FIG. 8, where some or all of the optical parts are disposed outside the vacuum specimen chamber, an external wall for separation between the inside of the vacuum specimen chamber and the atmosphere is located on an optical path. For allowing passage of light through the external wall, it is necessary to provide an entrance window made of transparent material such as glass. In an arrangement that the entrance window is formed along a plane of the external wall at the top of the vacuum specimen chamber as shown in FIG. 8, if a light beam is projected at a high angle of incidence in the light-reflected position detecting method, an incidence angle of the light beam to the entrance window becomes larger to increase reflectance on a surface of the entrance window significantly.

Figure 9:
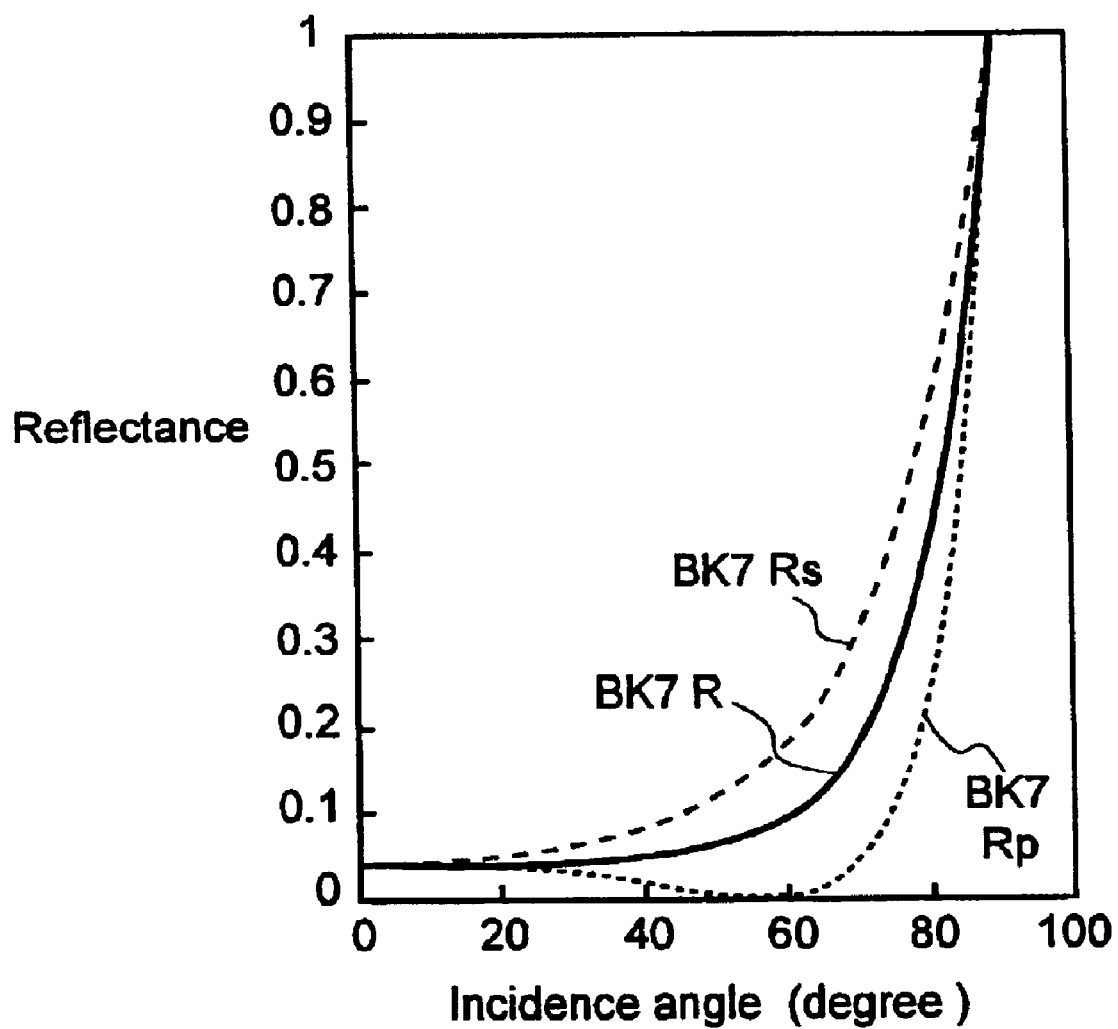
FIG. 9 is a graph showing variation in reflectance with respect to incidence angle on glass BK7.

Referring to FIG. 9, there is shown incidence angle dependency of surface reflectance of a representative kind of glass BK7 which is commonly used as an optical material. Since the surface of the entrance window may be coated with a conductive film and different kinds of window materials may be used, the incidence angle dependency will vary to some extent but its tendency characteristic is similar. As the incidence angle to the surface of the entrance window increases, a value of surface reflectance increases to cause larger loss in the quantity of light at passage through the entrance window.

As shown in FIG. 8, light may pass through two windows; an entrance window when it is projected onto a surface of a specimen, and an exit window after it is reflected therefrom. As the number of windows through which light passes is increased, loss in the quantity of light becomes larger. Further, in consideration of incidence angle distribution in the light beam (e.g., incidence angle distribution in a range of ±5.7 deg. in case of NA 0.1), it is required to avoid providing an incidence angle which causes significant variation in reflectance in order to prevent irregular distribution of the quantity of light in the beam.

Figure 10:
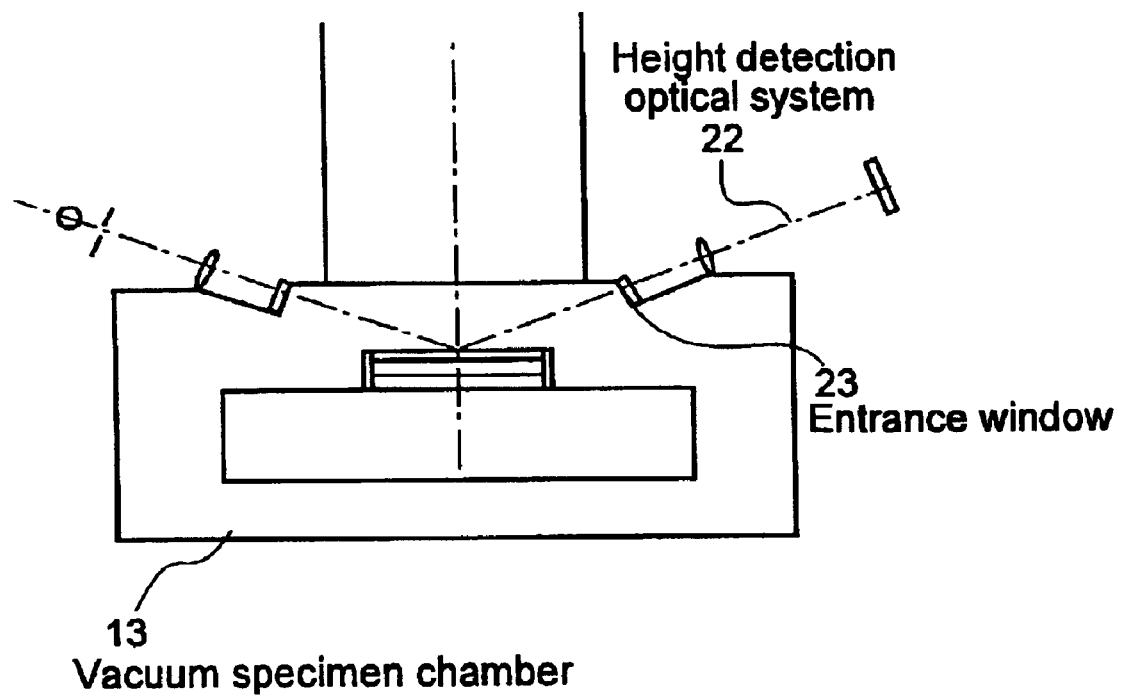
FIG. 10 is a schematic sectional view of a specimen chamber, showing an arrangement in which optical path windows are formed perpendicularly to an optical path on an external top wall of the specimen chamber.

Accordingly, as shown in FIG. 10, there may be provided such an arrangement that an entrance window 23 is formed perpendicularly to or at an angle which is almost perpendicular to the optical path of the height detection optical system for reducing surface reflectance on the window, thereby decreasing loss in the quantity of light on the optical path. In consideration of possible irregularity in distribution of the quantity of light in the beam, it is preferred to dispose the entrance window at an incidence angle of 30 deg. or less so that there will occur little variation in reflectance with incidence angle as indicated in FIG. 9. In addition to the external wall for separation between the inside of the vacuum specimen chamber and the atmosphere, there may be any member part on the optical path in the height detection optical system. If it is impossible to provide an opening through the member part, it is required to arrange a window thereon in the same manner. In such a case, loss in the quantity of light can be minimized by forming a shape of the window perpendicularly to the optical path as far as possible on condition that the shape of the window does not cause an adverse effect on the charged particle beam optical system.

Figure 11:
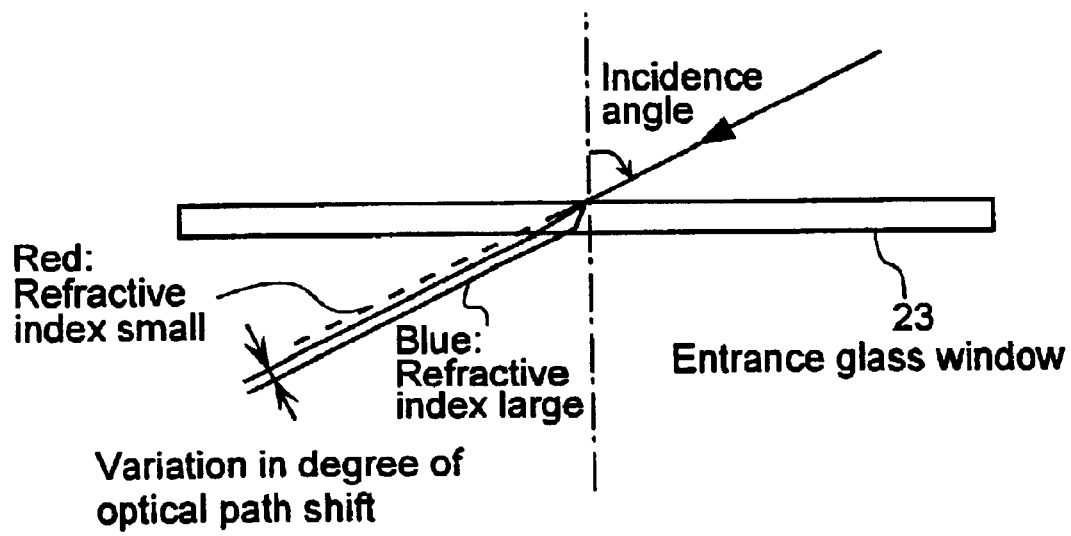
FIG. 11 is a schematic sectional view illustrating chromatic aberration due to a glass window.

The following description describes exemplary preferred embodiments for reducing an effect of chromatic aberration due to variance in refractive index of glass material used for a window for light passage. When a light beam for height detection passes though the window made of glass, its optical path is made to shift. As shown in FIG. 11, since there is variance in refractive index of glass material, a degree of optical path shift varies depending on wavelength. When white light is used for specimen surface height detection, an error may occur in height detection due to chromatic aberration caused by the white light.

Further, the degree of optical path shift is dependent on an angle of incidence and proportional to a thickness of glass plate. If the incidence angle to the glass plate of the window is decreased as in the foregoing preferred embodiment, the degree of optical path shift can be reduced. However, if the incidence angle is rather large, there arises a particular problem. (For example, in case that the incidence angle is 70 deg., glass BK7 is used and the thickness of glass plate is 2 mm, there occurs a difference of 9 μm in optical path shift between wavelengths of 656.28 nm and 404.66 nm.)

Where white light is used, an effect of chromatic aberration varies with color of an object under inspection and therefore its correction is rather difficult. For reduction in effect of chromatic aberration, there may be provided such arrangements that the window glass plate is made thinner and a glass plate for correcting chromatic aberration is inserted on the optical path. Since the degree of optical path shift is proportional to the thickness of window glass plate, it is preferred to use a glass plate having a thickness which will not cause significant chromatic aberration, in consideration of applicable wavelength coverage and desired accuracy of height detection.

It is not necessarily required to use glass material if a required strength can be satisfied, and therefore an optically transparent part made of pellicle material, for example, may be employed. However, in case of the window on the vacuum specimen chamber, considerable strength is required and it is not permitted to make the glass plate sufficiently thinner. Therefore, in such a case, the glass plate for correcting chromatic aberration may be inserted on the optical path.

Figure 12:
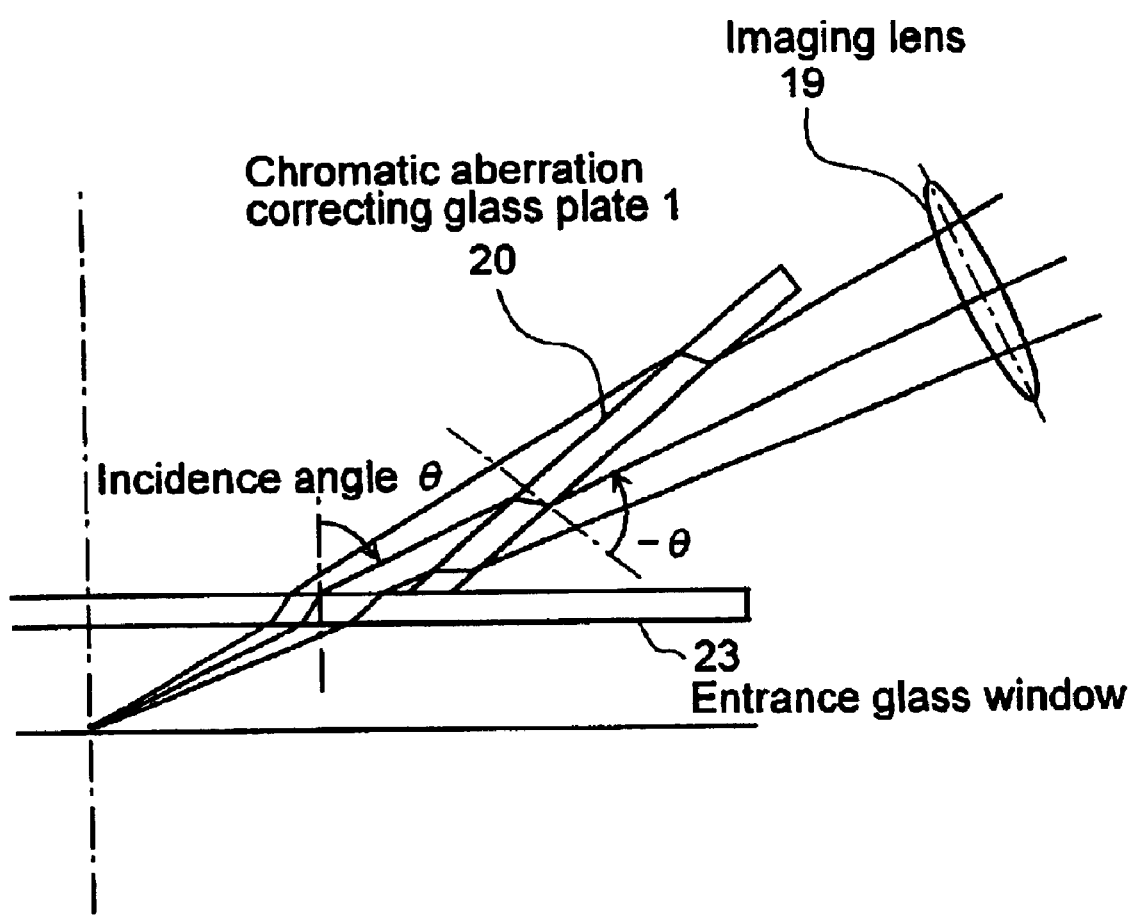
FIG. 12 is a schematic sectional view illustrating an arrangement in which a glass plate is inserted for correction of chromatic aberration due to a glass window.

Referring to FIG. 12, there is shown an arrangement that a chromatic aberration correcting glass plate is inserted in the same positional relation as that of an entrance window with respect to an imaging lens. In this arrangement, a difference in degree of optical path shift can be canceled by disposing the chromatic aberration correcting glass plate, which has the same characteristic as the entrance glass window in that it, for example, is made of the same material as that of the entrance window and has the same thickness as that of the entrance window, so that an incidence angle to the chromatic aberration correcting glass plate will be ? with respect to an incidence angle to the entrance glass window ?. A similar arrangement may also be provided on the detector side with respect to the exit glass window.

Figure 13:
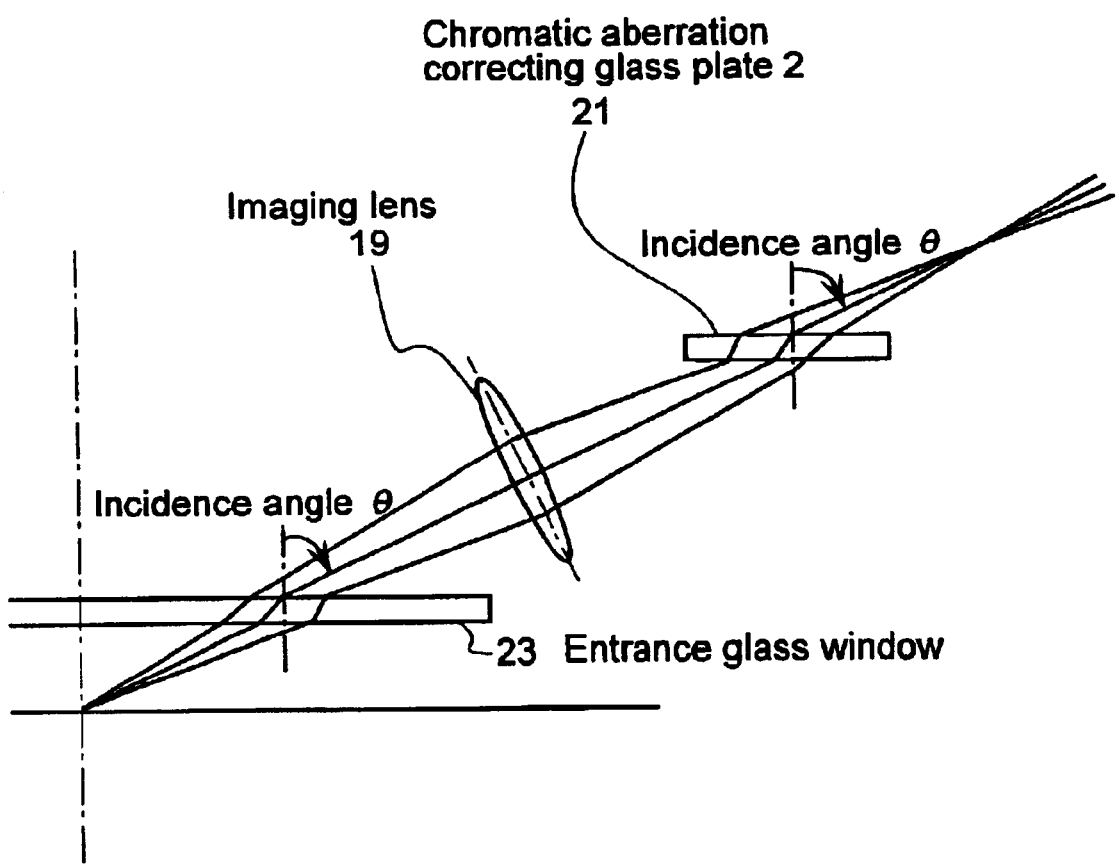
FIG. 13 is a schematic sectional view illustrating another arrangement in which a glass plate is inserted in a different manner for correction of chromatic aberration due to a glass window.

Further, in FIG. 13, there is shown an arrangement that a chromatic aberration glass plate and an imaging lens are located in reverse. In this arrangement, a difference in degree of optical path shift can also be canceled by disposing the chromatic aberration correcting glass plate, which is made of the same material as that of the entrance window and has a thickness proportional to a magnification of the imaging lens, so that the chromatic aberration correcting glass plate will be in parallel to the entrance window.

For the purpose of decreasing an accelerating voltage for the charged particle beam to be applied onto a specimen, a flat-plate electrode may be arranged at a position over a surface of the specimen in parallel thereto. In this arrangement, it is required to provide an opening or window on the flat-plate electrode to allow passage of light on an optical path for the height detector. Since a shape of the flat-plate electrode has an effect on electric field distribution in the vicinity of the specimen, it may affect the quality of charged particle beam images adversely. Exemplary embodiments for reducing an adverse effect on the charged particle beam images are described in the following description. A degree of adverse effect on the charged particle beam optical system varies depending on the size or position of the opening to be provided on the flat-plate electrode. An permissible level of adverse effect by the opening depends on performance required for the charged particle beam optical system. When the size of the opening is considerably small, its adverse effect may be negligible. Therefore, a method for reducing the opening size is explained below.

Figure 14:
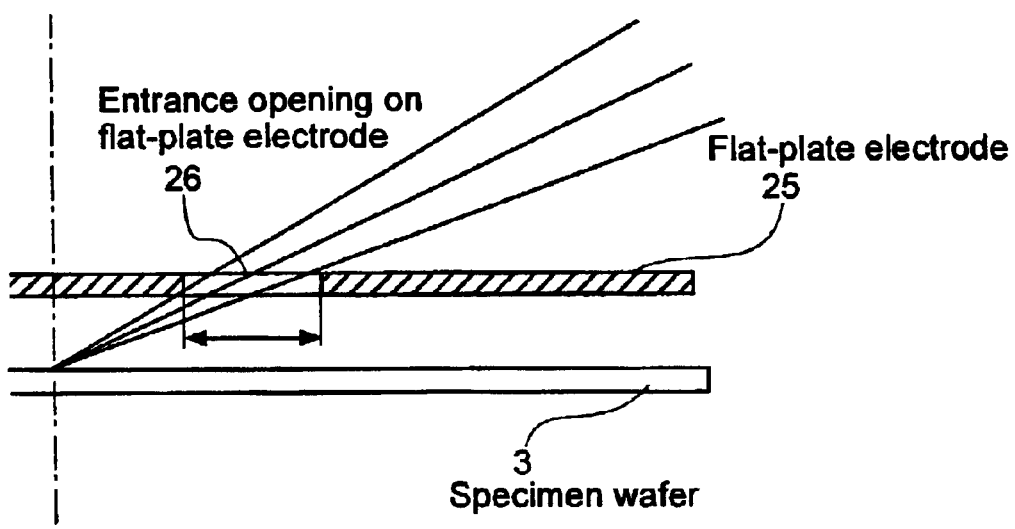
FIGS. 14(a) and (b) are schematic sectional views showing a change in optical path size on a flat-plate electrode according to incidence angle.
Figure 14:
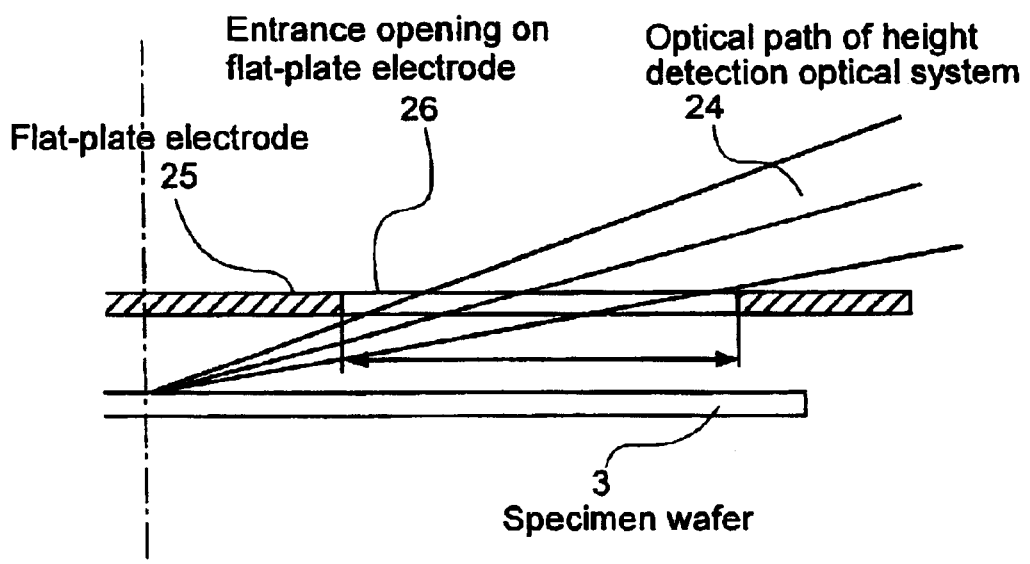

As shown in FIGS. 14(a) and 14(b), when an incidence angle to a surface of an object with respect to the vertical is increased from the small incidence angle of FIG. 14(a) to the relatively large incidence angle of FIG. 14(b), the size of an optical path going through a plane parallel to the object surface becomes larger even if a numerical aperture (NA) of the optical path of the height detection optical system is constant. Where the optical path goes through an opening on the flat-plate electrode as in this case, the shape of the opening 26 must be enlarged substantially in the projecting direction of the optical axis to the flat-plate electrode from that shown in FIG. 14(a) to that shown in FIG. 14(b). This gives rise to a problem particularly in a situation where the numerical aperture of the optical system is rather large and a distance between the flat-plate electrode and the object surface is rather long. A suitable position of the flat-plate electrode is determined according to specifications of the charged particle beam optical system, and it cannot be changed in common applications. Further, it is not allowed to extremely decrease the numerical aperture since a sufficient quantity of light must be provided for detection.

Reduction of the size of the opening without decreasing the entire quantity of light for detection is described below. Commonly, an optical lens aperture having a circular shape whose center coincides with the optical axis is employed. According to one aspect of the present invention, there is provided an elliptic or rectangular optical lens aperture having its major axis which is in the axial direction across the optical axis and parallel to the object surface and having its minor axis which is in the axial direction across the major axis and the optical axis. In this arrangement, the entire quantity of light necessary for height detection can be ensured by providing an elliptic or rectangular area which is equal to that of a circular lens aperture.

Figure 15:
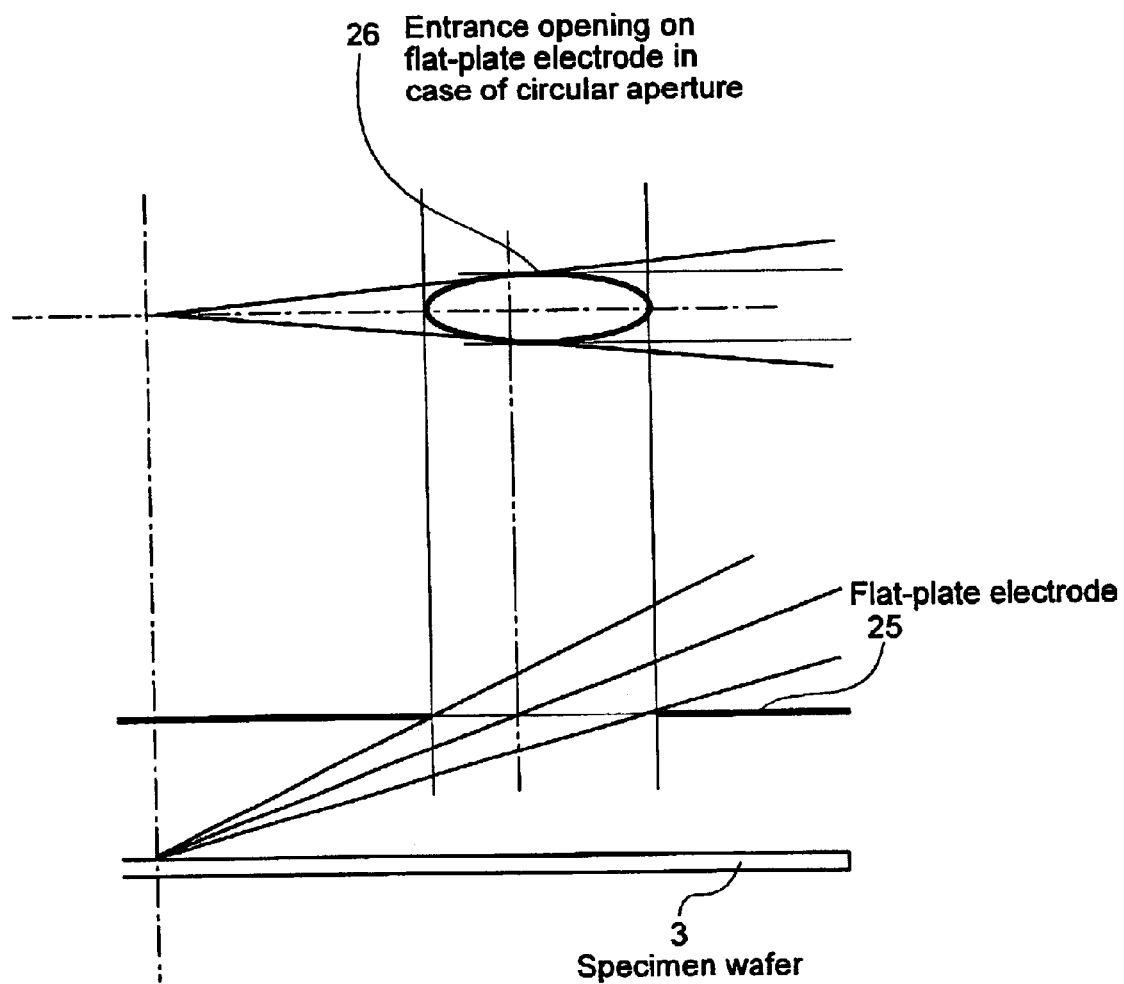
FIG. 15 is a schematic sectional view showing a shape of an entrance opening on the flat-plate electrode in case of a circular optical aperture.
Figure 16:
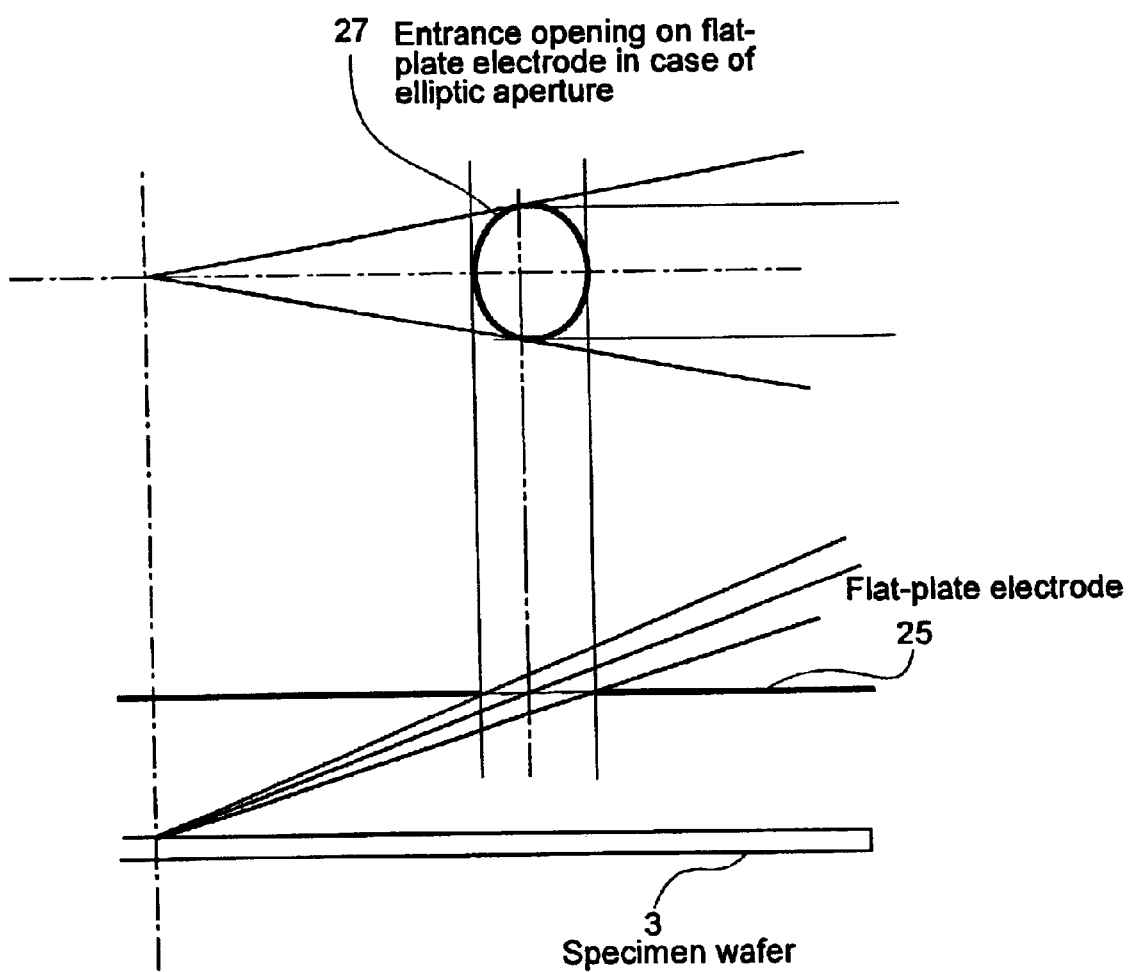
FIG. 16 is a schematic sectional view showing a shape of an entrance opening on the flat-plate electrode in case of an elliptical optical aperture.

FIG. 15 shows an optical geometry of an optical path going through the opening 26 of the flat-plate electrode 25 in case of a circular optical aperture, and FIG. 16 shows an optical geometry of an optical path going through the opening 26 of the flat-plate electrode 25 in case of an elliptical optical aperture which has almost the same area as that of the circular optical aperture in FIG. 15. As can be seen from these figures, the size of the opening 26 in one direction on the flat-plate electrode 25 can be reduced by using the elliptic aperture. As illustrated here, the size and shape of the opening can be changed by modifying the shape of the aperture as far as performance required for the height detector can be ensured. Thus, a degree of adverse effect on the charged particle beam optical system can be reduced.

Figure 17:
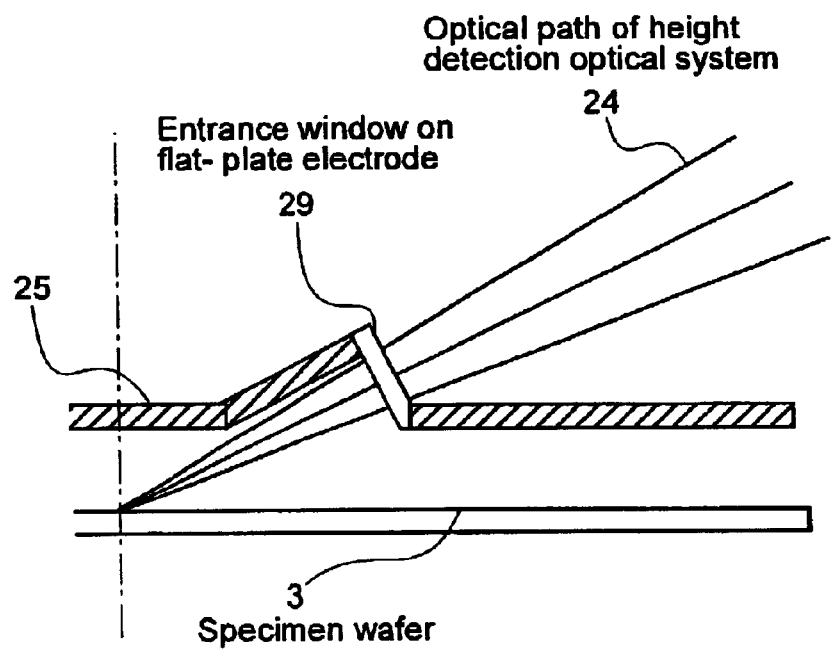
FIG. 17 is a schematic sectional view showing an example of an window formed perpendicularly to an optical path on the flat-plate electrode.

If the charged particle beam optical system is affected by the size of the opening so that performance required for it cannot be attained, it is necessary to provide a further measure. For example, instead of merely a hollow opening formed on the flat-plate electrode, there may be provided such an arrangement that a window made of glass coated with a conductive film or other material is formed on the flat-plate electrode to allow passage of light on an optical path. In this arrangement, an adverse effect due to electric field to be given to an object or its periphery can be reduced. As exemplified in FIG. 8, if the window is formed at the position of the opening along a plane of the flat-plate electrode in FIG. 14, significant loss in the quantity of light occurs due to reflection on a surface of the window, causing irregular distribution in the quantity of light in the beam. Therefore, as exemplified in FIG. 10, there may be provided such an arrangement that the window is formed perpendicularly to or at an angle almost perpendicular to the optical path. Thus, loss in the quantity of light due to reflection on the surface of the window can be decreased. FIG. 17 shows an example of the window formed in this arrangement.

The opening or window formed on the flat-plate electrode in the foregoing examples has a considerable effect on electric potential distribution in the vicinity of the object. The following describes an opening/window disposition method for reducing this effect. Since the window and opening can be disposed in the same manner, the window is taken in the description given below.

In a microstructure observation/fabrication system to which the present invention is directed, two-dimensional observation or fabrication is mostly carried out through two-dimensional scanning by deflecting a convergent charged particle beam or through stage scanning by combination of one-dimensional scanning based on charged particle beam deflection and stage movement in the direction orthogonal to the one-dimensional scanning. According to the present invention, the window is disposed in consideration of charged particle beam deflection and stage movement direction in charged particle beam scanning. Thus, an effect of variation in electric field due to the window can be reduced as proposed below.

Figure 18:
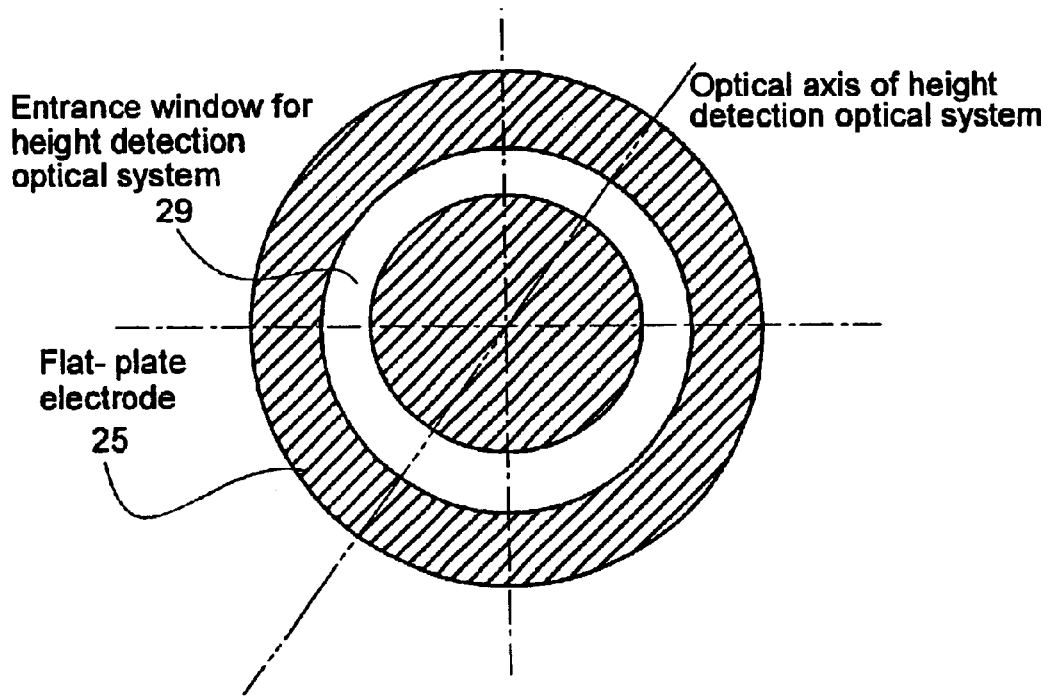
FIG. 18 is a schematic top view showing an example of disposition in which a window is provided in a circumferential form symmetrically with respect to an optical axis of an electron beam optical system.
Figure 19:
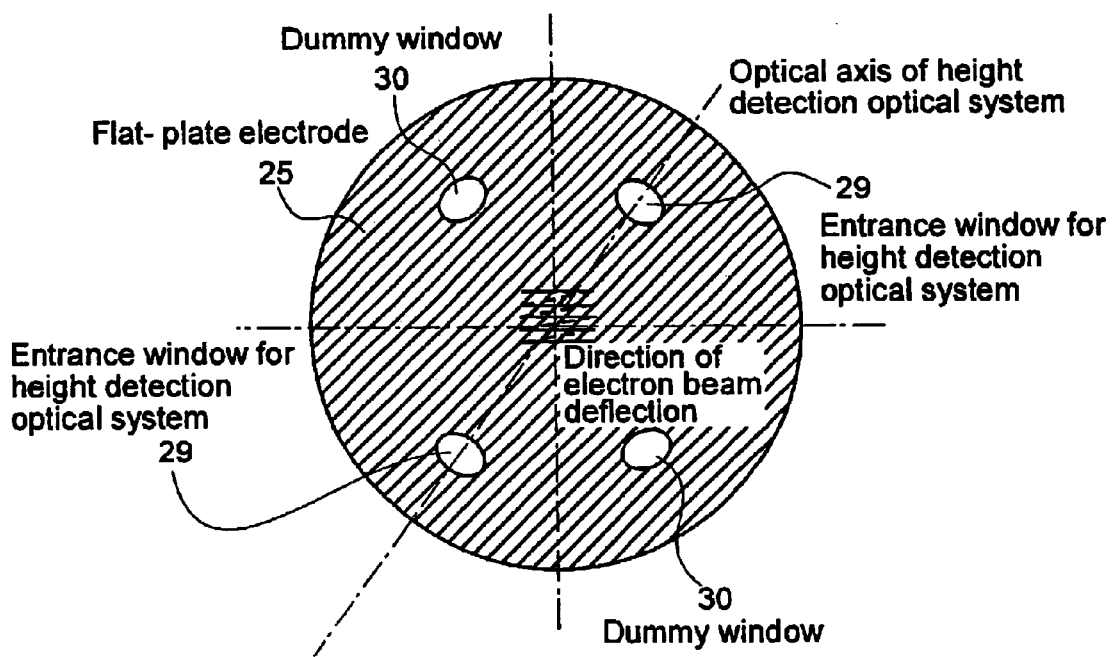
FIG. 19 is a schematic top view showing an example of disposition in which windows are provided symmetrically with respect to an axis of deflection direction.

Referring to FIG. 18, there is shown an example of disposition in which the window 29 is provided in a circumferential form having its center at the optical axis of the charged particle beam optical system. Since the window is located at a position apart from a scanning range of the charged particle beam, an effect of variation in electric field due to the window is isotropic in the disposition shown in FIG. 18. Thus, the effect will be almost uniform in an observation region in the charged particle beam optical system. Further, it is possible to attain almost the same result by disposing dummy windows 30 at axisymmetric positions with respect to the directions of electron beam deflection and stage movement as shown in FIG. 19.

Figure 20:
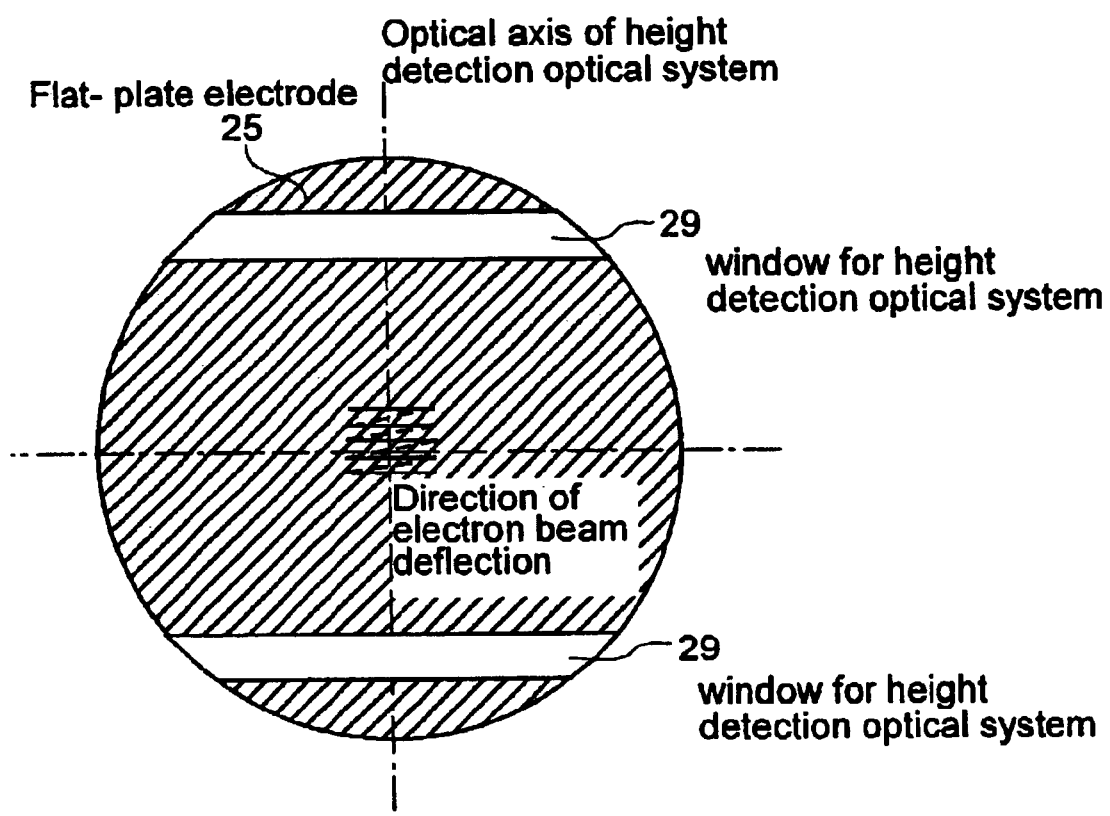
FIG. 20 is a schematic top view showing another example of disposition in which windows are provided in a parallel form symmetrically with respect to an axis of deflection direction.

In case of stage scanning, electric field distribution in a deflection range can be made uniform by disposing windows 29 in parallel to the deflection direction as shown in FIG. 20. If electric field distribution is kept uniform, scanning position correction is allowed to enable improvement in image quality. In carrying out the present invention, an effect to be given by the shape and disposition of these windows or openings is to be examined in consideration of specifications of the charged particle beam optical system and desired inspection performance to select suitable window formation and disposition.

The following describes exemplary embodiments for charged particle beam focus adjustment using height detection result data attained by the height detector. A focal point of the charged particle beam is adjusted by an objective lens control current. Using input data of an object surface height detected by the height detector in an observation region of the charged particle beam optical system, the objective lens control current is regulated to enable observation of a charged particle beam image which is always in focus. For this purpose, in the charged particle beam optical system, a level of objective lens control current is to be calibrated beforehand with respect to variation in object surface height. Further, an offset and gain in relation between the height detector and the charged particle beam optical system are to be calibrated beforehand.

Calibration methods for offset and gain will be described in the following exemplary embodiments. When the charged particle beam optical system is not structured in a telecentric optical arrangement, variation in object surface height will cause a magnification error in addition to a defocused condition. As to the magnification error, correction can be made through feedback control of a deflection circuit using height variation data, thus making it possible to always attain a charged particle beam image at the same magnification. Further, if the microstructure observation/fabrication system using the convergent charged particle beam is provided with a mechanism capable of moving an object in the Z-axis direction with high accuracy and at response speed sufficient for focal point control, resultant data of height detection may be used for object stage height feedback control instead of feedback control of the charged particle beam optical system.

Where stage height feedback control is carried out, a surface of the object can always be maintained at a constant height with respect to the height detector and the charged particle beam optical system. Therefore, no problem will arise even if a guaranteed detection accuracy range of the height detector is narrow. As a drive mechanism for an object stage, there may be provided a piezoelectric mechanism enabling fine movement at high speed under vacuum, for example. When such a piezoelectric mechanism is used, a magnification error does not occur since a height of the object surface is always maintained at a constant level with respect to the charged particle beam optical system.

Calibration of objective lens control current and focal point in the charged particle beam optical system may be carried out in the following manner. In an instance where there is a nonlinear relationship between objective lens control current and focal point, it is required to make correction for nonlinearity. Linearity evaluation and correction value determination may be effected as described below.

Figure 21:
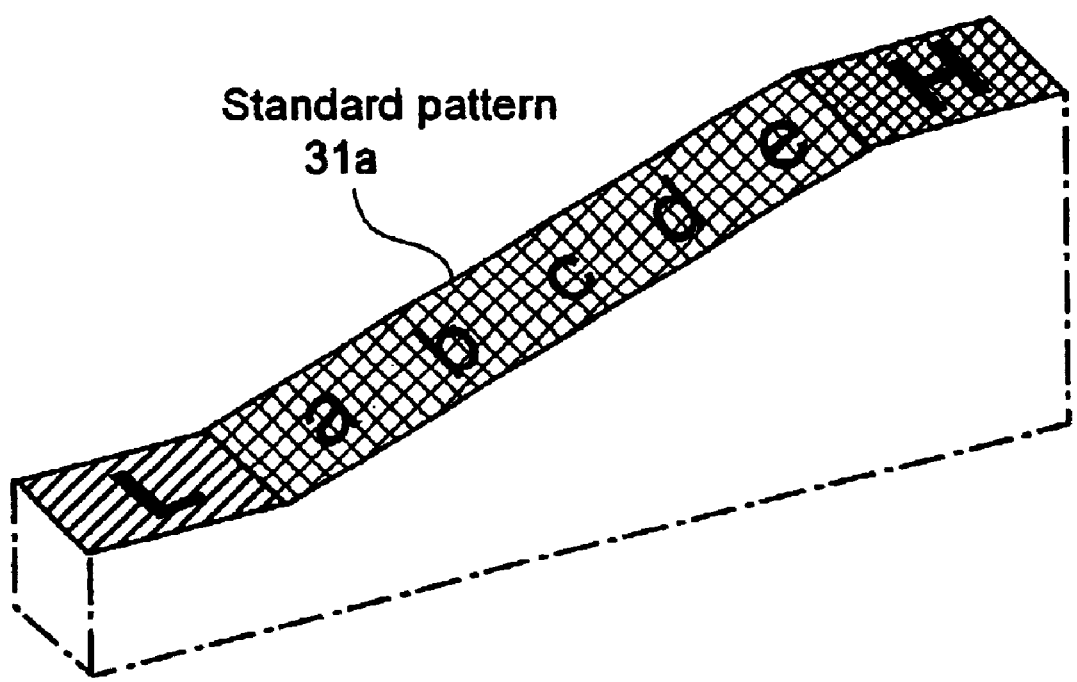
FIG. 21 is a perspective view of a standard calibration pattern having a slope part.
Figure 22:
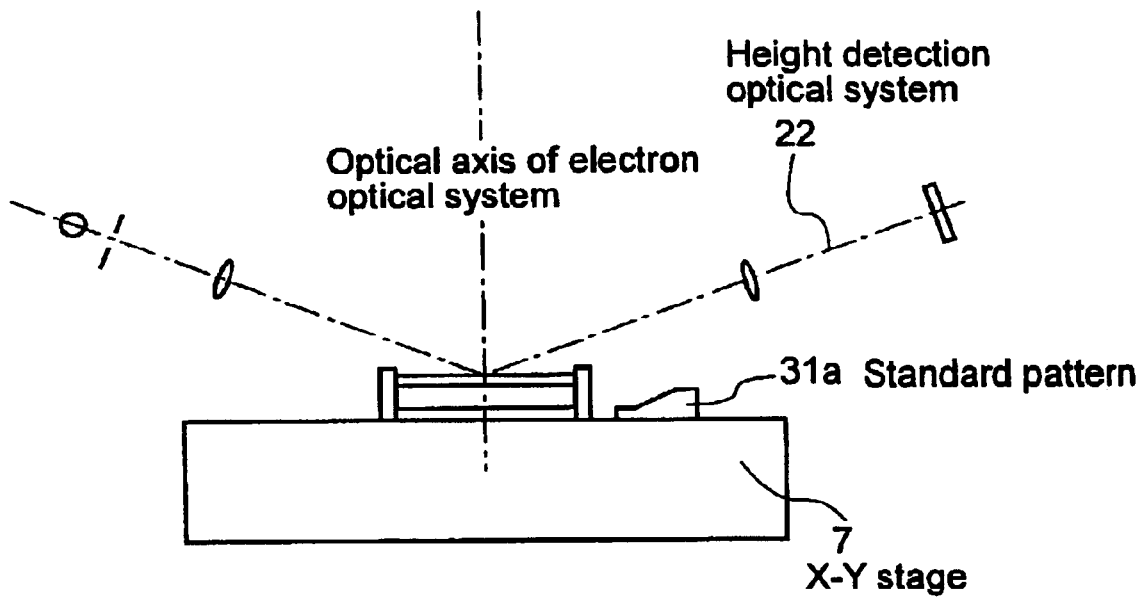
FIG. 22 is a schematic section view showing an automatic inspection system in which the standard calibration pattern is secured to an X-Y stage.

Referring to FIG. 21, there is shown a standard pattern 31a for calibration. As shown in FIG. 22, this standard calibration pattern is secured to a stage for holding an object. The standard calibration pattern is made of conductive material so that it will not be charged by scanning of the charged particle beam. It is also desirable to provide such a surface pattern feature that a height at each position can be identified.

Figure 23:
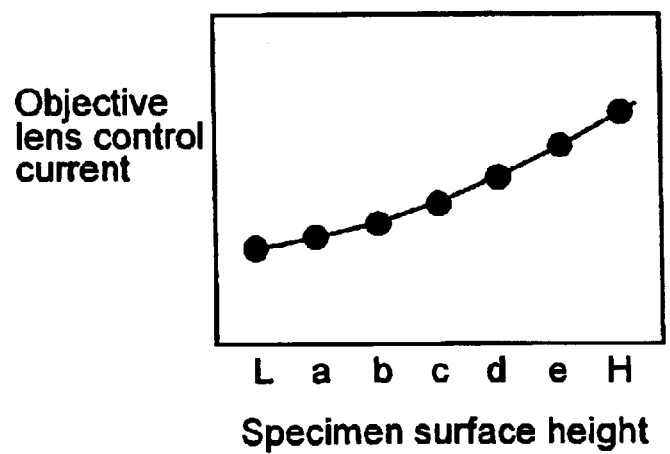
FIG. 23 is a graph for explaining a relationship between objective lens control current and specimen surface height.

When the object holding stage is movable on a plane as in the inspection system shown in FIG. 2, the standard pattern is moved to an observation region at the time of calibration. Using the standard pattern, objective lens control current measurement is effected to determine a current level where a charged particle beam image becomes sharpest at each point. At this step, visibility of the charged particle beam image is determined through visual observation or image processing. In this measurement, it is possible to determine a relationship between variation in object surface height and optimum level of objective lens control current as shown in FIG. 23. If the relationship between variation in object surface height and optimum level of objective lens control current is determined, a value of objective lens control current which is most suitable for forming the charged particle beam image in focus can be identified using object surface height data attained by the height detector.

Figure 24:
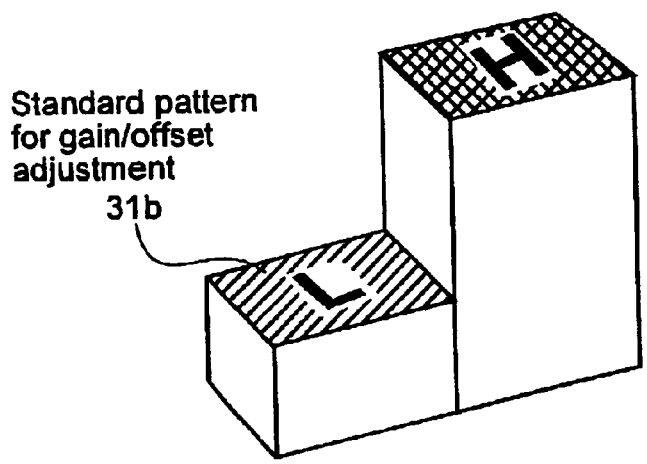
FIG. 24 is a perspective view of a standard calibration pattern having two step parts.

The standard pattern 31a shown in FIG. 21 has a flat part at both ends thereof. At each flat part, if a reference height is determined through measurement with the optical height detector, gain/offset calibration of objective lens control current can be made according to height measurement data. In case that characteristics of objective lens control current and focal point are calibrated for the objective lens by any means, gain/offset calibration of objective lens control current may be made with respect to the optical height detector using a standard pattern 31b which has two step parts as shown in FIG. 24.

Where the object holding stage is not provided with a movement mechanism, the charged particle beam optical system can be calibrated by disposing the standard pattern so that it will always be located in a visual field of the charged particle beam optical system. Further, the standard pattern may be formed so that it can be attached to an object holding jig. Thus, even when the object holding stage is not provided with a movement mechanism, it is possible to perform calibration by setting the standard pattern on the stage and thereafter exchange the standard pattern with the object for observation.

Figure 25:
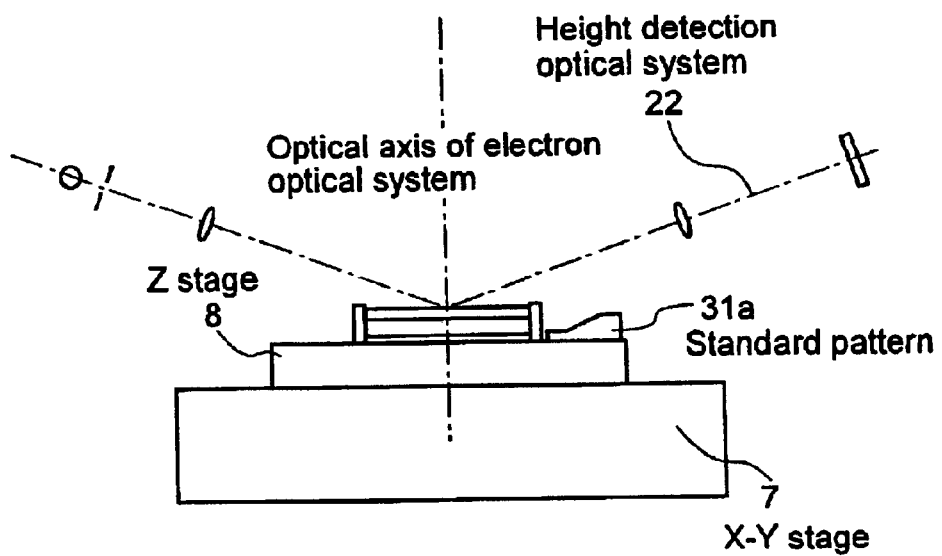
FIG. 25 is a schematic sectional view showing an automatic inspection in which the standard calibration pattern is mounted on a Z stage.

In case that the charged particle beam system is provided with a mechanism for moving an object in the height direction as shown in FIG. 25, an ordinary stepless pattern is utilizable instead of the standard pattern shown in FIG. 21. Through height detection by Z stage movement and image evaluation using the stepless pattern, calibration of objective lens control current can be made with respect to the height detector. Where there is provided a movement mechanism for Z stage, it is possible to conduct focus adjustment using the Z stage. However, if a response speed of the Z stage is not sufficiently high for an observation region change speed, focal adjustment may be made using the objective lens control current with the stage being fixed.

Calibration of the charged particle beam optical system using the standard pattern shown in FIG. 21 is practicable only in a microstructure observation/inspection system which allows observation of a surface feature of the standard pattern using the charged particle beam optical system. As contrasted, in a microstructure fabrication system, calibration is to be made only for the height detector using the standard step-pattern shown in FIG. 24, and for a relationship between focal point and control current of the charged particle beam optical system, calibration is made beforehand therein. Where the microstructure fabrication system is provided with a charged particle beam image observation mode in which such an operational parameter as an accelerating voltage for the convergent charged particle beam can be altered, it is possible to check a point detected by the height detector using a charged particle beam image.

Figure 26:
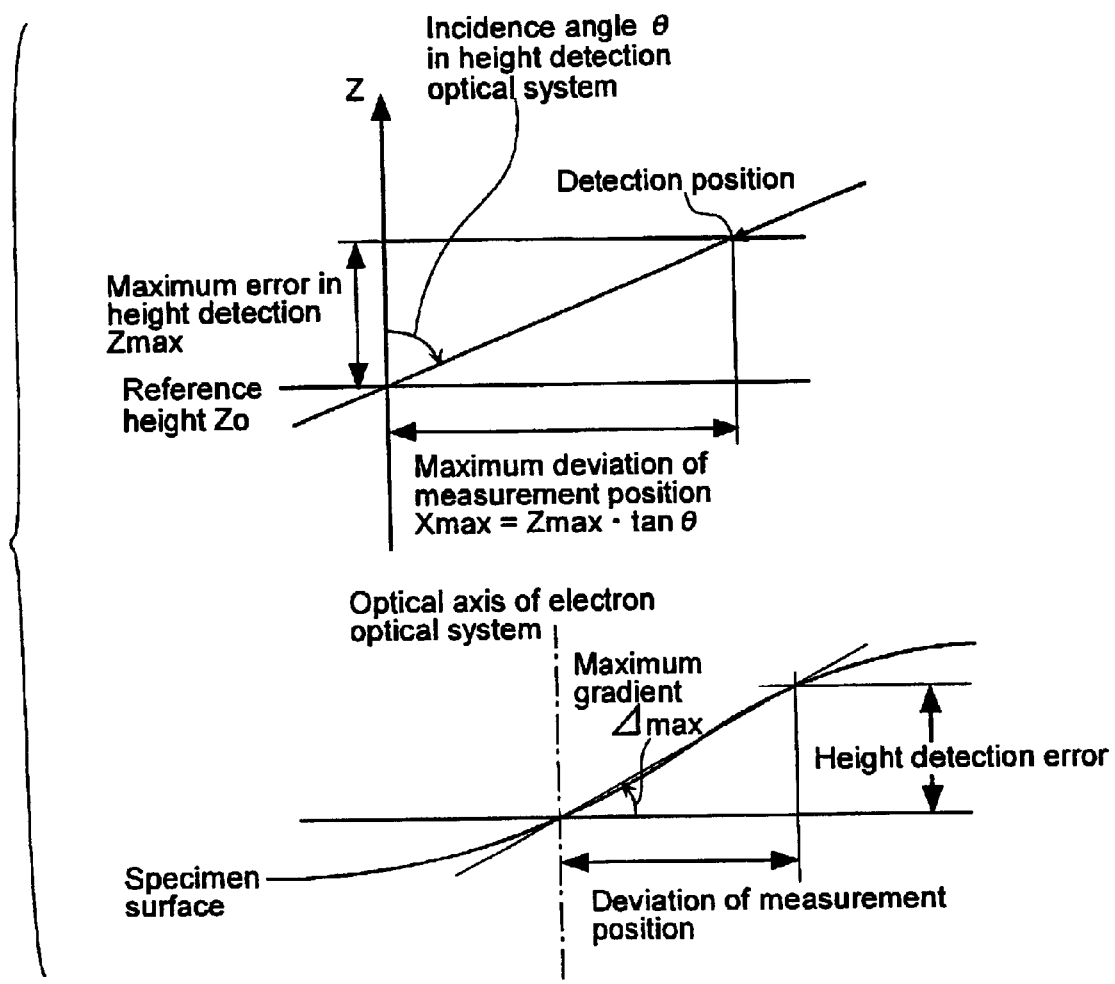
FIG. 26 shows a relationship between deviation in measurement position and error in height detection.

The following describes exemplary embodiments concerning focal point correction and relationship between height measurement position under inspection and observation position in the charged particle beam optical system. If the observation position of the charged particle beam optical system completely meets the height detection position of the height detector, focus adjustment may be made according to height data detected by the height detector. However, in the light-reflected position detecting method, a deviation of detection position occurs due to variation in object surface height as illustrated in FIG. 3. Designating a predictable value of maximum variation in object surface height as Zmax and an incidence angle in the height detection optical system as θ, a value of maximum positional deviation Xmax is equal to Zmax·tan φ. Then, on condition that a value of allowable variation in object surface height in terms of focal depth of the charged particle beam optical system and performance requirement for the system is z0 and a predictable value of maximum gradient of object surface is Δmax, a value of height detection error for maximum positional deviation dz is expressed as Δmax·Xmax=Δmax·Zmax·tan θ as indicated in FIG. 26. If the height detection error dz is smaller than z0, there arises no problem. However, if dz is larger than z0, it is required to attain a height on the optical axis of the charged particle beam optical system.

Figure 27:
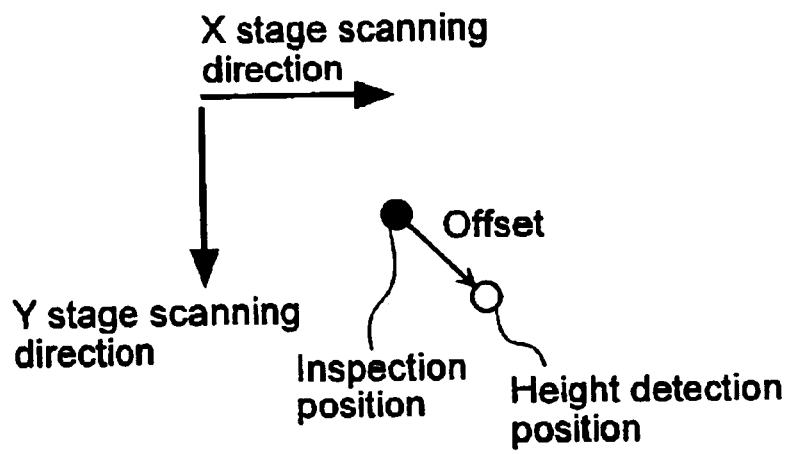
FIGS. 27(a) and (b) show views of a specimen surface for explaining a method of presuming an observation region height using height data detected continuously.
Figure 27:
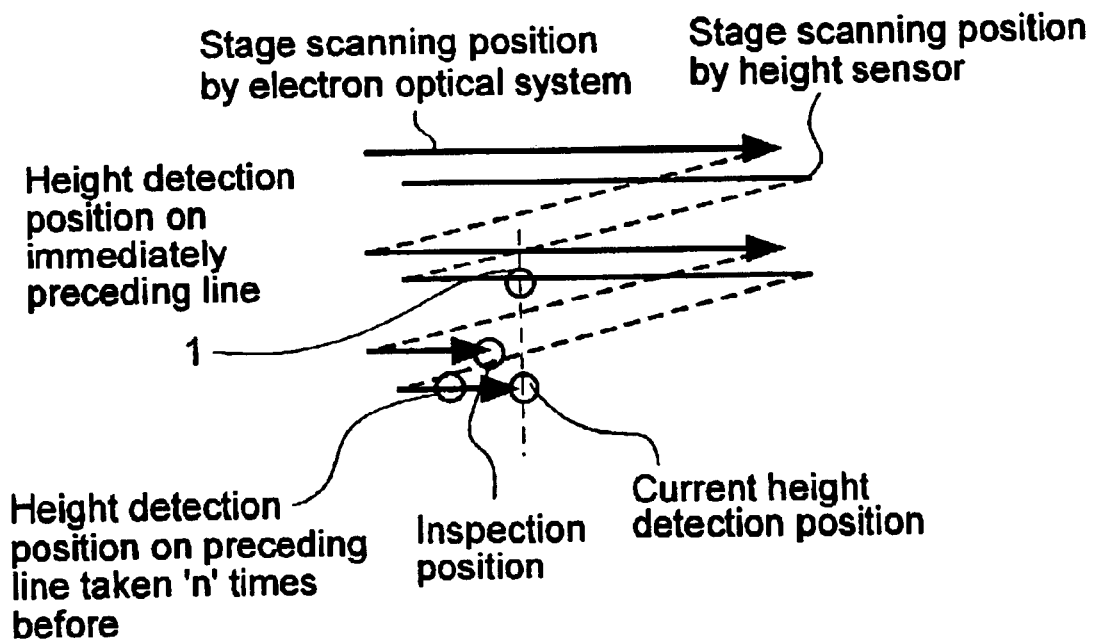

In the inspection system according to the present invention, since continuous inspection is performed by moving the stage, height data at each point can be attained continuously. Using resultant data of height detection, a height of object surface in an observation region in the charged particle beam optical system may be presumed or predicted to enable focus adjustment. Focus adjustment when there is a positional deviation between the height detection position and the observation region in the charged particle beam optical system may be effected in the following manner. In the following description, it is assumed that stage scanning is performed by deflecting the beam of the charged particle beam optical system in the Y-axis direction and moving the stage in the X-axis direction to produce a two-dimensional image.

Where each of X-axis and Y-axis stage scanning movements is always limited to one direction at the time of inspection, if each of the X-axis and Y-axis scanning movements is always made in one direction only as shown in FIG. 27, i.e., reciprocal scanning movement is not performed, the height detector may be disposed with an offset so that the height detection position will always be located before the observation position of the charged particle beam optical system with respect to the direction of stage scanning movement as shown in FIG. 27(a). In this manner, a height at a desired position can be determined using height data in the vicinity of the observation region, which is attainable before each step of inspection.

As shown in FIG. 27(b), three points in the vicinity of the current inspection position are selected and a height of the inspection position is presumed according to a local plane determined by these three points. It is necessary to select three points so that the current inspection position will be located inside a triangle formed with the selected three points. Thus, a height of the inspection position can be presumed reliably through interpolation. In this case, although a height of a stage scanning position at the start of inspection cannot be presumed, it can be determined by performing a sequence of scanning for height detection in advance.

Figure 28:
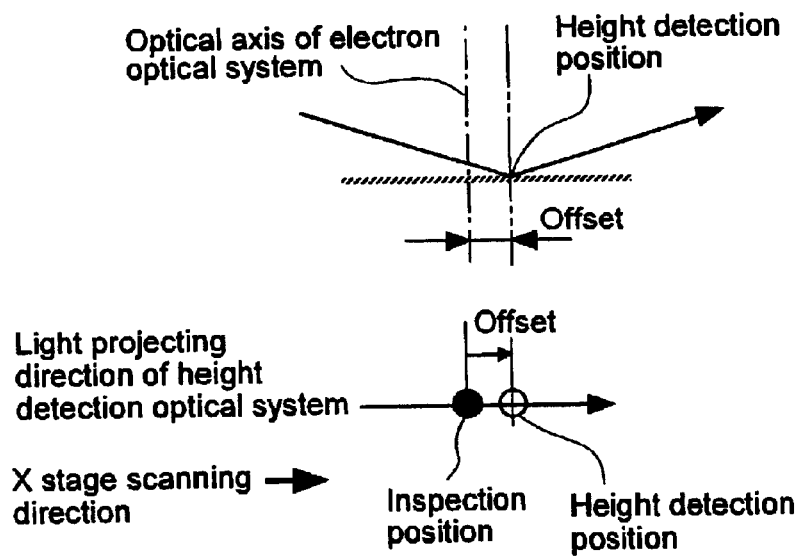
FIGS. 28(a)–(c) show views of a specimen surface for explaining a method of presuming an observation region height using height data detected continuously.
Figure 28:
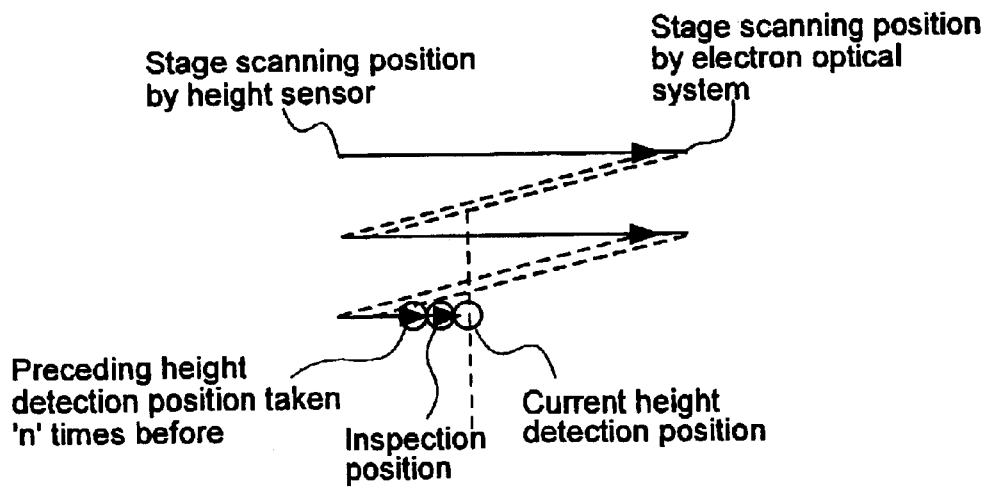
Figure 28:
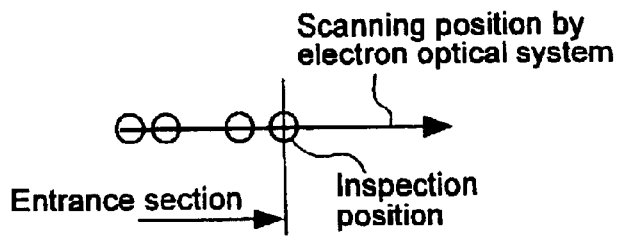

Another exemplary embodiment is considered in that either one of X-axis and Y-axis stage scanning movements is always limited to one direction and also the axis movable only in one direction coincides with the projection direction of the height detection optical system. As shown in FIG. 28, if the X-axis stage scanning movement is always limited to one direction and the X axis coincides with the projection direction of the height detection optical system, positional deviation in height detection due to variation in height takes place only in the X-axis direction. Therefore, by providing an offset in the X-axis direction as shown in FIG. 28(a), a height can be determined through one-dimensional interpolation using height data on one line only. In this case, a height of the inspection position may be determined by means of linear interpolation using two-point data or spline interpolation using three-point data. At the start of inspection, a height detection value in an entrance section until the stage reaches a constant speed may be used.

Figure 29:
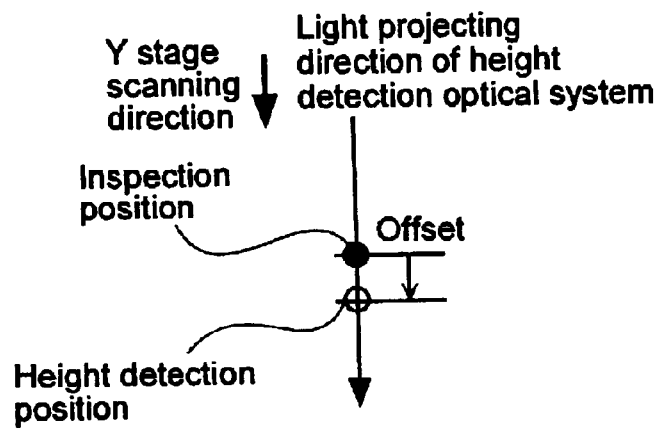
FIGS. 29(a) and (b) show views of a specimen surface for explaining a method of presuming an observation region height using height data detected continuously in a different manner.
Figure 29:
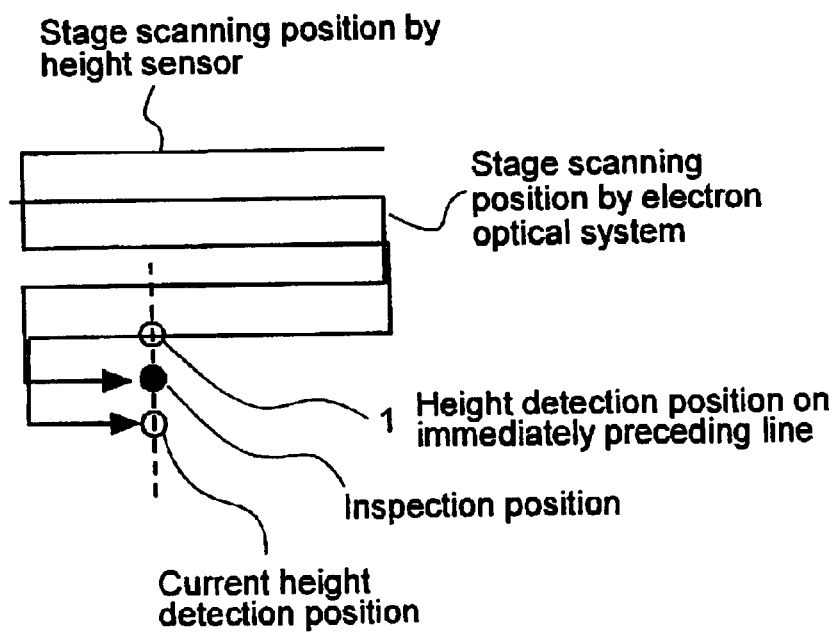

Further, as shown in FIG. 29, if the Y-axis stage scanning movement is always limited to one direction and the Y axis corresponds to the projection direction of the height detection optical system, positional deviation in height detection due to variation in height takes place only in the Y-axis direction. Therefore, by providing an offset in the Y-axis direction as shown in FIG. 29(a), a height of the inspection position can always be determined reliably through interpolation using height detection data on a preceding line. In case that the stage is moved in a reciprocal scanning fashion, such an offset as mentioned above cannot be provided in one direction.

Figure 30:
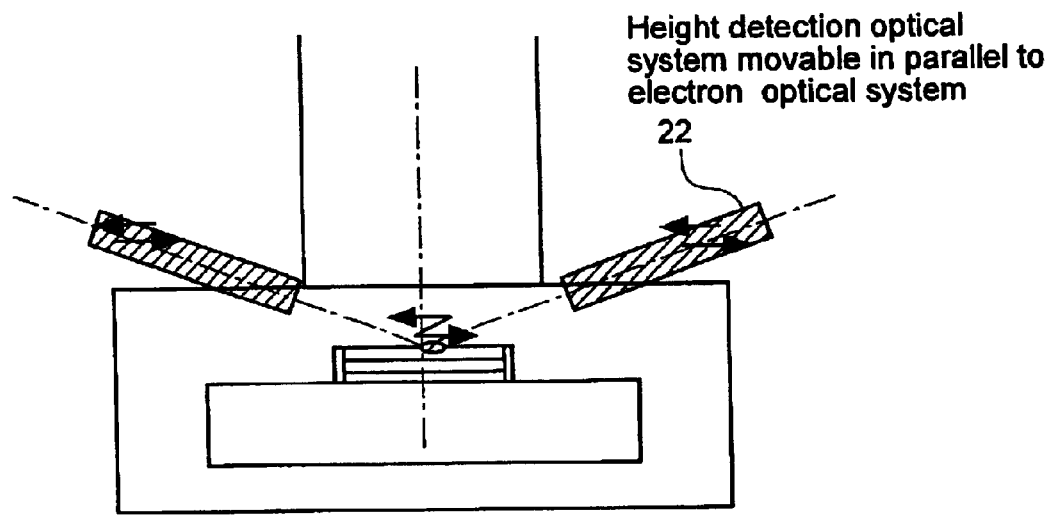
FIG. 30 is a schematic sectional view of a specimen chamber in which a height detection optical system can be moved in parallel to an electron optical system.

In an arrangement that the optical axis of the charged particle beam optical system is made to coincide with a reference position of height detection, it is possible to presume a height of the inspection position using height detection data attained. However, since a height of the inspection position cannot always be determined through interpolation, its reliability is not ensured. For reliable height detection, there may be provided such an arrangement that the height detection optical system is equipped with a movable mechanism and the entire optical-system is shifted in parallel as shown in FIG. 30 so as to give an offset in the stage scanning movement direction. Thus, a height of the inspection position can always be determined reliably through interpolation in the same manner as in the foregoing example. There may also be provided such an arrangement that a plurality of height detectors are disposed to enable height measurement at a plurality of points in the vicinity of the inspection position. In this arrangement, data of only necessary points can be used according to the stage scanning movement direction.

Figure 31:
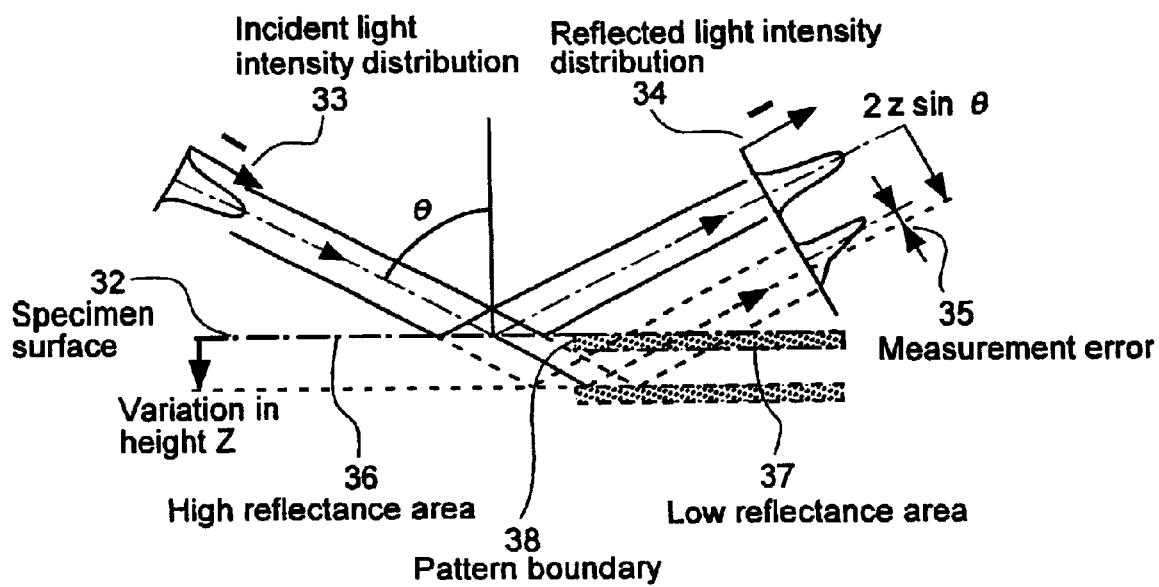
FIG. 31 is a schematic section view of a specimen for explaining a height detection error due to nonuniform reflectance on a specimen surface.
Figure 32:
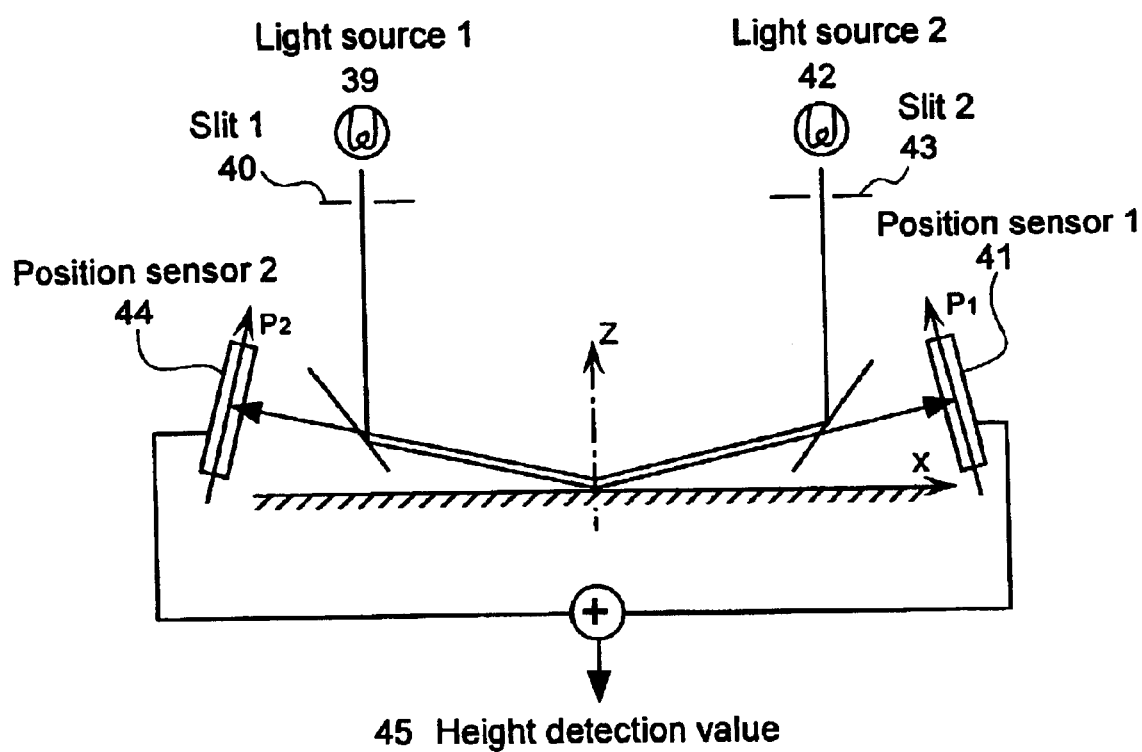
FIG. 32 is a schematic sectional view of an optical system in which two slit light beams are projected symmetrically for detection.

Exemplary embodiments for optical height detection in which a height of a specimen surface can be detected reliably without being affected by a state of the specimen surface are now considered. In case that a specimen surface height is detected by the light-reflected position detecting method as shown in FIG. 3, a deviation of a detection position occurs to cause an error in height detection. As shown in FIG. 31, if a specimen surface 32 is provided with pattern areas having different reflectances (high reflectance area 36, low reflectance area 37) and slit light is projected onto a pattern boundary 38 therebetween, reflected light intensity distribution 34 of slit light to be detected is affected to cause an error in height detection. Such a height detection error may be reduced in the following manner. As shown in FIG. 32, two slit light beams are projected onto the specimen surface in directions symmetrical with respect to a normal line thereon, and respective reflected light beams from the specimen surface are detected. If sensors for detecting these slit light beams are disposed as shown in FIG. 32, a light image shift due to variation in specimen surface height is made in the same direction and a measurement error due to specimen surface features appears in the opposite directions. Therefore, an effect of specimen surface pattern features can be canceled by means of addition. Further, in case that the slit light beams are projected in two directions as shown in FIG. 32, a deviation of the detection position due to variation in height occurs to the same extent in the opposite directions. Therefore, a deviation of the detection position can be eliminated by means of averaging.

Figure 33:
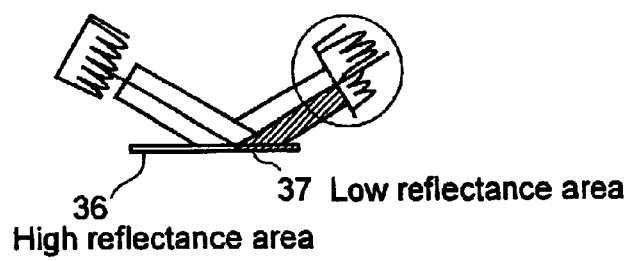
FIGS. 33(a)–(c) show diagrams for explaining height detection using a plurality of fine slit light beams.
Figure 33:
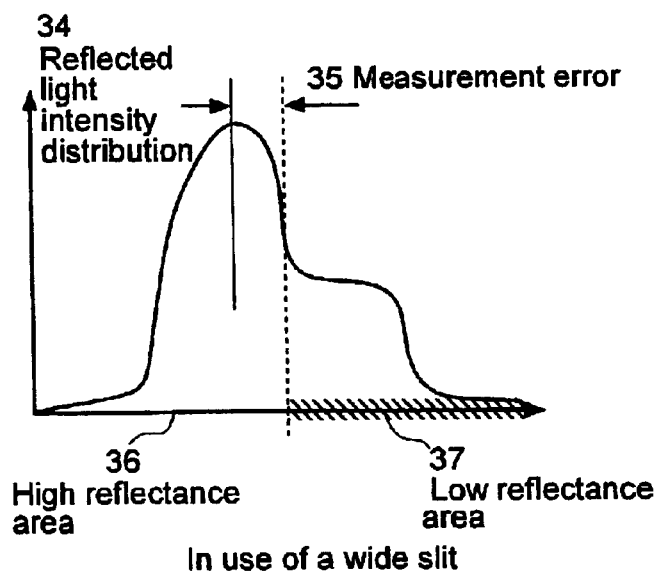
Figure 33:
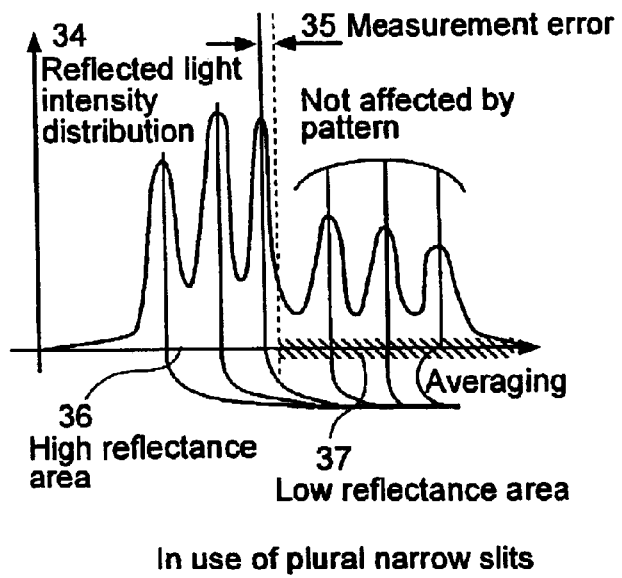

FIG. 33 shows a method for reducing an effect of specimen surface pattern features using a plurality of fine slits. A height detection error due to specimen surface pattern features increases in proportion to a slit width. Therefore, as shown in FIG. 33(a), a plurality of fine slit light beams are projected onto the specimen surface, and reflected light beams are detected by a linear image sensor. Individual center values of plural slit beam images are determined and averaged, thus making it possible to reduce an error in height detection. As shown in FIG. 33(c) in comparison with FIG. 33(b), an error on a pattern boundary can be reduced by decreasing each slit width. Since fine slit beams on other than the pattern boundary are not affected by pattern features, an error on the pattern boundary can be decreased through averaging. Although the quantity of light to be detected decreases as each slit width is decreased, an S/N ratio can be improved by averaging for plural slit positions, thereby ensuring reliability in height detection.

According to the present invention, it is possible to detect a height of an observation position in the electron beam optical system using the optical height detector and attain an in-focus electron beam image while conducting inspection. In an electron beam inspection system, inspection performance and reliability thereof can be improved by carrying out inspection using an electron beam image which is always focused in a consistent state. Furthermore, since height detection can be made simultaneously with inspection, continuous stage movement is applicable to inspection to reduce a required inspection time substantially. This feature is particularly advantageous in inspection of semiconductor wafers which will become still larger in diameter in the future. Similarly, the same advantageous effects can be attained in a microstructure observation/fabrication system using a convergent charged particle beam. Further, by disposing the height detection optical system outside the vacuum specimen chamber, adjustment and maintenance can be carried out with ease.

While we have shown and described several embodiments in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

What is claimed is:

1. A convergent charged particle beam apparatus comprising:

an electron beam system which emits a converged electron beam;

a vacuum chamber which is connected to the electron beam system and which has an exhausting unit to maintain an inside of the vacuum chamber at a predetermined vacuum atmosphere;

a stage which mounts a specimen and moves at least in one direction inside of the vacuum chamber;

an electron beam image observation unit which observes an electron beam image of a surface of the specimen mounted on the stage by irradiation of the electron beam emitted from the electron beam system and scanned over the surface of the specimen;

a height detector which optically detects a height of the specimen mounted on the stage by illuminating the surface of said specimen with light at an incident angle of at least 60 degree and by detecting a reflected light of the illumination reflected from the surface of the specimen; and a controller which controls a focus position of the electron beam in accordance with an output from the height detector while the stage is moving at least in one direction.

2. A convergent charged particle beam apparatus according to the claim 1, wherein the height detector detects a height of a surface of the specimen in a region irradiated with the electron beam.

3. A convergent charged particle beam apparatus according to the claim 1, wherein the height detector illuminates the surface of the specimen from outside of the vacuum chamber and detects a light reflected from the specimen outside of the vacuum chamber.

4. A convergent charged particle beam apparatus according to the claim 1, further comprising an image processor which processes the electron beam image observed by the electron beam image observation unit and detects a defect on the surface of the specimen.

5. A method of detecting an electron beam image of a specimen comprising the steps of:

irradiating a converged electron beam on a surface of a specimen mounted on a table and scanning the electron beam in a scanning direction on the surface of the specimen;

moving the table in one direction substantially perpendicular to the scanning direction of the electron beam;

detecting a height of the surface of the specimen mounted on the moving table;

controlling a focus position of the converged electron beam which is irradiated and scanned on the surface of the specimen in accordance with information of height of the surface of the specimen detected at the detecting step;

observing an electron beam image of the surface of the specimen mounted on the moving table by the irradiation and scanning of the electron beam;

processing the electron beam image obtained at the observing step; and displaying on a display screen the electron beam image of the surface of the specimen processed by the processing step.

6. A method according to the claim 5, wherein in the step of detecting a height, the height of the surface of the specimen in a region irradiated with the electron beam is detected.

7. A method according to the claim 5, wherein in the step of detecting a height, the height of the surface of the specimen is detected by illuminating light on the surface at an incident angle of at least 60 degrees and by detecting a reflected light of the illumination light reflected from the surface of the specimen.

8. A method according to the claim 5, further comprising the step of detecting a defect on the surface of the specimen by using the electron beam image processed at the processing step.

* * * * *